US009216122B2

(12) United States Patent
Dzioba et al.

(10) Patent No.: US 9,216,122 B2
(45) Date of Patent: Dec. 22, 2015

(54) SUPPORT APPARATUS, SYSTEM AND METHOD

(75) Inventors: David A. Dzioba, Frankenmuth, MI (US); Kenneth A. Wolf, Chesterfield Township, MI (US); Timothy Wyrick, Quincy, IL (US)

(73) Assignee: TOUCHSENSOR TECHNOLOGIES, LLC, Wheaton, IL (US)

(*) Notice: Subject to any disclaimer, the term of this patent is extended or adjusted under 35 U.S.C. 154(b) by 273 days.

(21) Appl. No.: 13/253,869

(22) Filed: Oct. 5, 2011

(65) Prior Publication Data

US 2012/0079662 A1   Apr. 5, 2012

Related U.S. Application Data

(60) Provisional application No. 61/390,016, filed on Oct. 5, 2010, provisional application No. 61/535,294, filed on Sep. 15, 2011.

(51) Int. Cl.
| | | |
|---|---|---|
| *A47C 27/10* | (2006.01) | |
| *A61G 7/057* | (2006.01) | |
| *A61H 9/00* | (2006.01) | |
| *A47C 21/04* | (2006.01) | |

(52) U.S. Cl.
CPC ............ *A61G 7/05776* (2013.01); *A47C 27/10* (2013.01); *A61H 9/0078* (2013.01); *A47C 21/042* (2013.01); *A61G 2007/05792* (2013.01); *A61H 2201/0146* (2013.01); *A61H 2209/00* (2013.01)

(58) Field of Classification Search
CPC .... A47C 21/04; A47C 21/042; A47C 21/046; A47C 27/002; A47C 27/081; A47C 27/082; A47C 27/10; A61G 7/05776; A61G 7/05769; A61G 2007/05784; A61G 2007/05792; A61H 9/0078; A61H 2201/0146; A61H 2209/00
USPC .................. 5/644, 706, 654, 655.3, 710–714; 297/284.6, 452.1, DIG. 3; 601/148, 149
See application file for complete search history.

(56) References Cited

U.S. PATENT DOCUMENTS

| | | |
|---|---|---|
| 1,274,851 A | 8/1918 | Byrd |
| 2,604,758 A | 7/1952 | Swindler |
| 2,719,986 A | 10/1955 | Rand |

(Continued)

FOREIGN PATENT DOCUMENTS

| | | |
|---|---|---|
| DE | 4201460 | 7/1993 |
| EP | 0025701 | 3/1981 |

(Continued)

OTHER PUBLICATIONS

International Search Report and Written Opinion for Int'l Pat. Appl. No. PCT/US2011/038928, dated Nov. 11, 2011.

(Continued)

*Primary Examiner* — Nicholas Polito
(74) *Attorney, Agent, or Firm* — Barnes & Thornburg LLP

(57) ABSTRACT

A therapeutic support device includes a bladder having one or more independently inflatable compartments, each including a plurality of inflatable cells. When inflated, each inflatable cell forms a contact node that may support a user or another object disposed thereon. The inflatable compartments can be alternately inflated and deflated such that contact pressure can be applied to and relieved from corresponding portions of the user's body in an alternating manner.

26 Claims, 29 Drawing Sheets

(56) References Cited

U.S. PATENT DOCUMENTS

| | | | |
|---|---|---|---|
| 3,148,391 A * | 9/1964 | Whitney | 5/422 |
| 3,199,124 A | 8/1965 | Grant | |
| 3,303,518 A | 2/1967 | Ingram | |
| 3,390,674 A | 7/1968 | Jones | |
| 3,483,862 A | 12/1969 | Takeuchi | |
| 3,674,019 A | 7/1972 | Grant | |
| 3,678,520 A | 7/1972 | Evans | |
| 3,701,173 A | 10/1972 | Whitney | |
| 3,784,994 A | 1/1974 | Kery | |
| 3,919,730 A | 11/1975 | Regan et al. | |
| 3,970,077 A | 7/1976 | Dahl | |
| 4,037,591 A | 7/1977 | Sarno | |
| 4,175,297 A | 11/1979 | Robbins et al. | |
| 4,267,611 A * | 5/1981 | Agulnick | 5/713 |
| 4,391,009 A | 7/1983 | Schild et al. | |
| 4,472,847 A | 9/1984 | Gammons et al. | |
| 4,524,762 A | 6/1985 | Schulman | |
| 4,559,656 A | 12/1985 | Foster | |
| 4,653,130 A | 3/1987 | Senoue et al. | |
| 4,840,425 A | 6/1989 | Noble | |
| D315,188 S | 3/1991 | Thomas | |
| 4,999,861 A | 3/1991 | Huang | |
| 5,010,608 A | 4/1991 | Barnett et al. | |
| 5,035,016 A | 7/1991 | Mori et al. | |
| 5,060,326 A | 10/1991 | Oswald | |
| 5,103,518 A | 4/1992 | Gilroy et al. | |
| 5,109,558 A | 5/1992 | Di Blasi | |
| 5,117,518 A | 6/1992 | Schild | |
| 5,135,282 A | 8/1992 | Pappers | |
| 5,210,889 A | 5/1993 | Wesemann et al. | |
| 5,235,710 A | 8/1993 | Nagashima | |
| 5,243,723 A | 9/1993 | Cotner | |
| D341,983 S | 12/1993 | Wang | |
| 5,267,365 A | 12/1993 | Walter | |
| 5,437,068 A | 8/1995 | Fisher | |
| 5,447,491 A | 9/1995 | Bellandi | |
| 5,487,196 A | 1/1996 | Wilkinson et al. | |
| 5,542,136 A | 8/1996 | Tappel | |
| 5,638,565 A * | 6/1997 | Pekar | 5/710 |
| 5,659,910 A | 8/1997 | Weiss | |
| 5,678,265 A | 10/1997 | Meyer | |
| 5,685,036 A | 11/1997 | Kopfstein et al. | |
| 5,687,438 A | 11/1997 | Biggie et al. | |
| 5,729,853 A | 3/1998 | Thompson | |
| 5,755,000 A | 5/1998 | Thompson | |
| 5,820,573 A | 10/1998 | Ramos | |
| 5,901,393 A | 5/1999 | Pepe et al. | |
| 5,963,997 A | 10/1999 | Hagopian | |
| 5,970,550 A | 10/1999 | Gazes | |
| 6,014,784 A | 1/2000 | Taylor et al. | |
| 6,098,222 A | 8/2000 | Hand et al. | |
| 6,151,740 A | 11/2000 | Morimoto et al. | |
| 6,178,578 B1 | 1/2001 | Soltani et al. | |
| 6,216,299 B1 | 4/2001 | Kohlman | |
| 6,241,695 B1 | 6/2001 | Dabir | |
| 6,336,907 B1 | 1/2002 | Dono et al. | |
| 6,378,152 B1 | 4/2002 | Washburn et al. | |
| 6,383,153 B2 | 5/2002 | Dabir | |
| D471,051 S | 3/2003 | Cook | |
| D474,061 S | 5/2003 | Cook et al. | |
| 6,668,405 B1 | 12/2003 | Kohlman | |
| 6,687,935 B2 | 2/2004 | Reeder et al. | |
| 6,689,077 B2 | 2/2004 | Dabir | |
| 6,711,771 B2 | 3/2004 | Cook et al. | |
| D490,635 S | 6/2004 | Boso | |
| 6,823,549 B1 | 11/2004 | Hampton et al. | |
| 6,829,797 B2 | 12/2004 | Partian | |
| 6,910,238 B2 | 6/2005 | Biggie et al. | |
| 6,912,749 B2 | 7/2005 | Thomas et al. | |
| 7,037,278 B2 | 5/2006 | Dabir | |
| 7,159,255 B2 | 1/2007 | Piraino | |
| D537,287 S | 2/2007 | Lau | |
| 7,191,482 B2 | 3/2007 | Romano et al. | |
| 7,328,472 B2 | 2/2008 | Chaffee | |
| 7,392,557 B1 | 7/2008 | Kohlman | |
| 7,409,735 B2 | 8/2008 | Kramer et al. | |
| 7,520,011 B1 | 4/2009 | Liberkowski | |
| 7,562,409 B2 | 7/2009 | Chan | |
| 7,784,130 B2 | 8/2010 | Pile | |
| 8,051,516 B2 * | 11/2011 | Carlson et al. | 5/710 |
| 2002/0133105 A1 | 9/2002 | Dabir | |
| 2004/0231051 A1 | 11/2004 | Jansen | |
| 2006/0117488 A1 | 6/2006 | Hung et al. | |
| 2006/0150327 A1 | 7/2006 | Jansen | |
| 2007/0033738 A1 | 2/2007 | Tu | |
| 2008/0034501 A1 | 2/2008 | Hyde et al. | |
| 2008/0040861 A1 | 2/2008 | Ootayopas | |
| 2008/0178392 A1 | 7/2008 | Chu | |
| 2008/0188781 A1 | 8/2008 | Carkner et al. | |
| 2009/0193590 A1 | 8/2009 | Hata | |
| 2010/0024132 A1 | 2/2010 | Carlson et al. | |
| 2010/0205750 A1 | 8/2010 | McCausland et al. | |
| 2010/0263131 A1 | 10/2010 | Kajiwara et al. | |
| 2011/0107521 A1 * | 5/2011 | Alder et al. | 5/706 |

FOREIGN PATENT DOCUMENTS

| | | |
|---|---|---|
| GB | 2107197 | 4/1983 |
| GB | 2197192 | 5/1988 |
| WO | 03/022197 | 3/2003 |
| WO | 2004/096108 | 11/2004 |

OTHER PUBLICATIONS

International Search Report and Written Opinion for Int'l Pat. Appl. No. PCT/US2011/054982, dated Jan. 18, 2012.

* cited by examiner

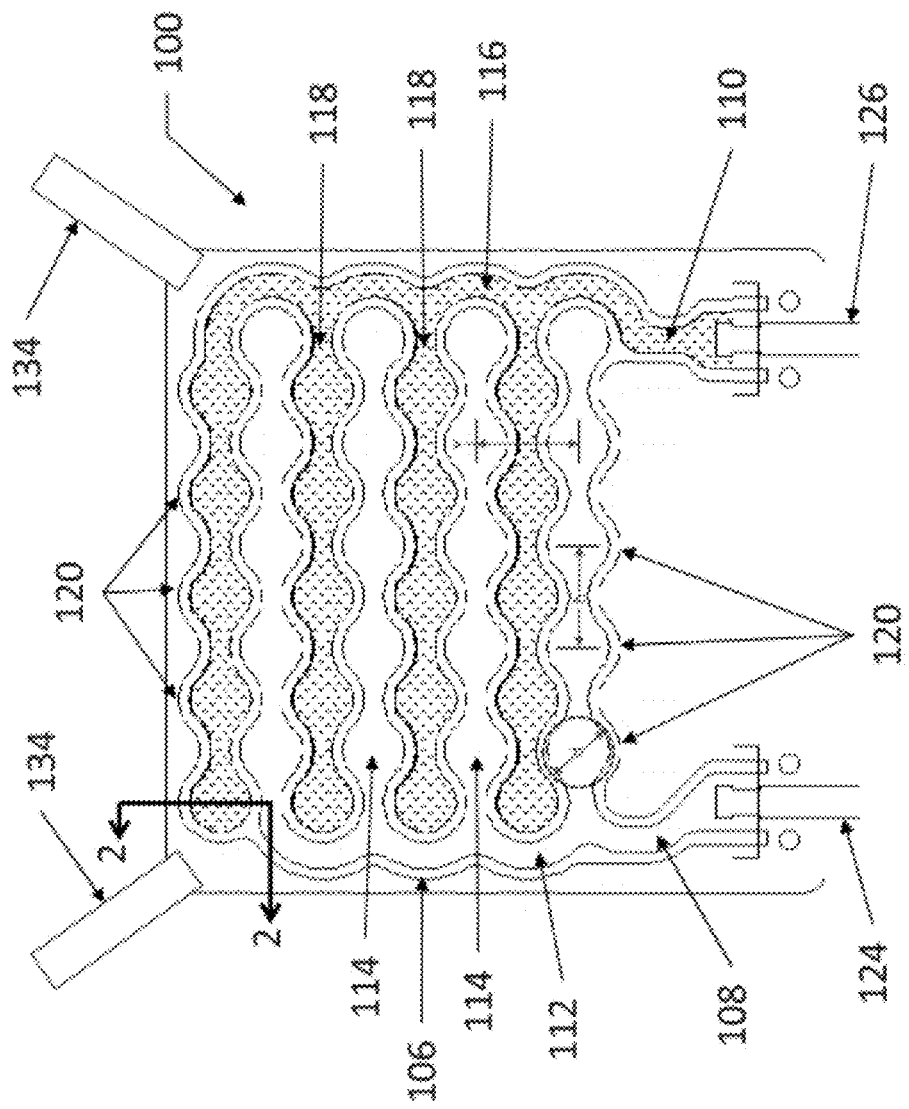

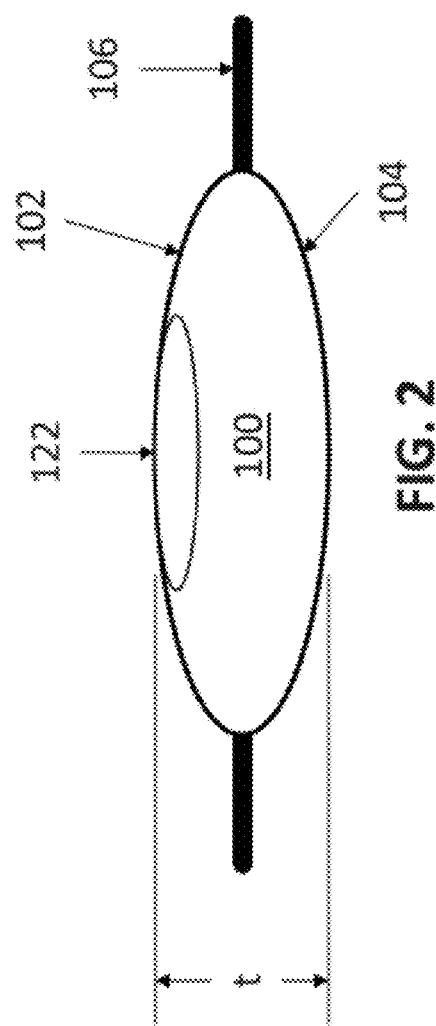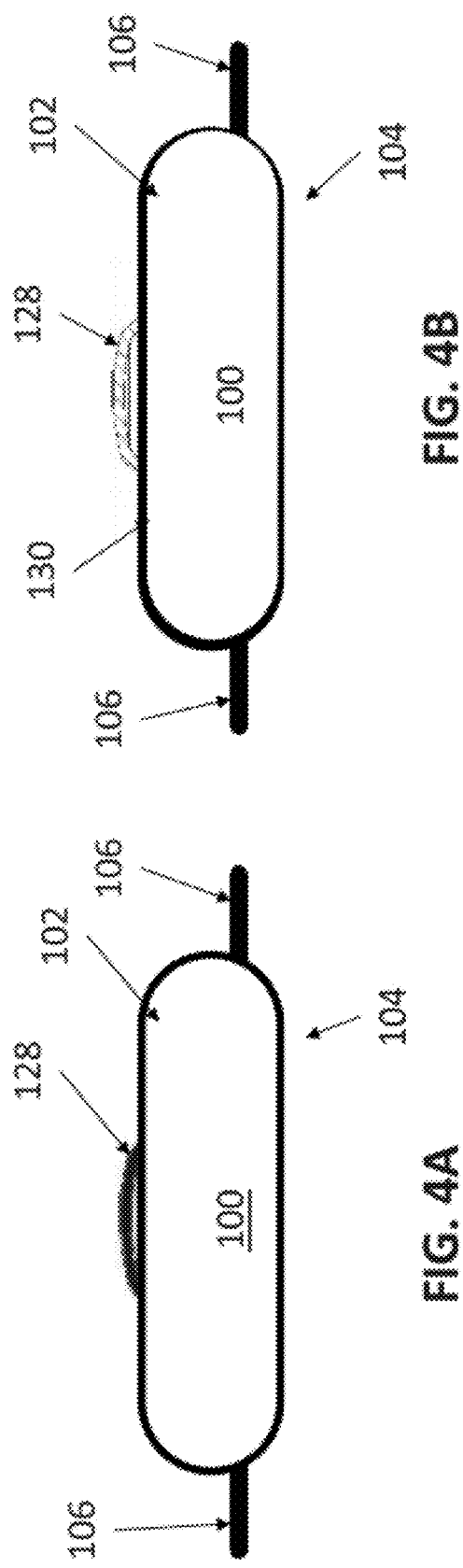

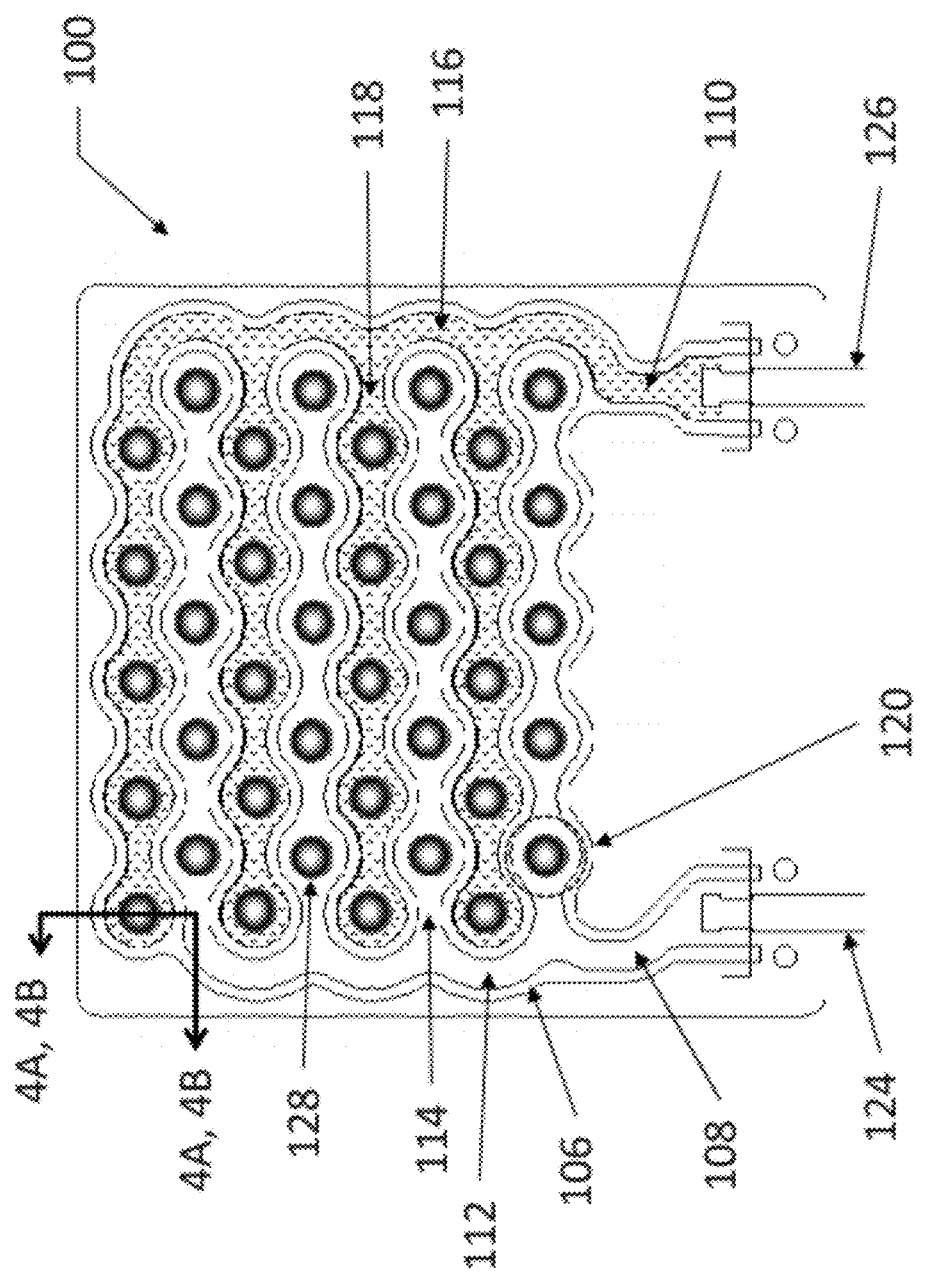

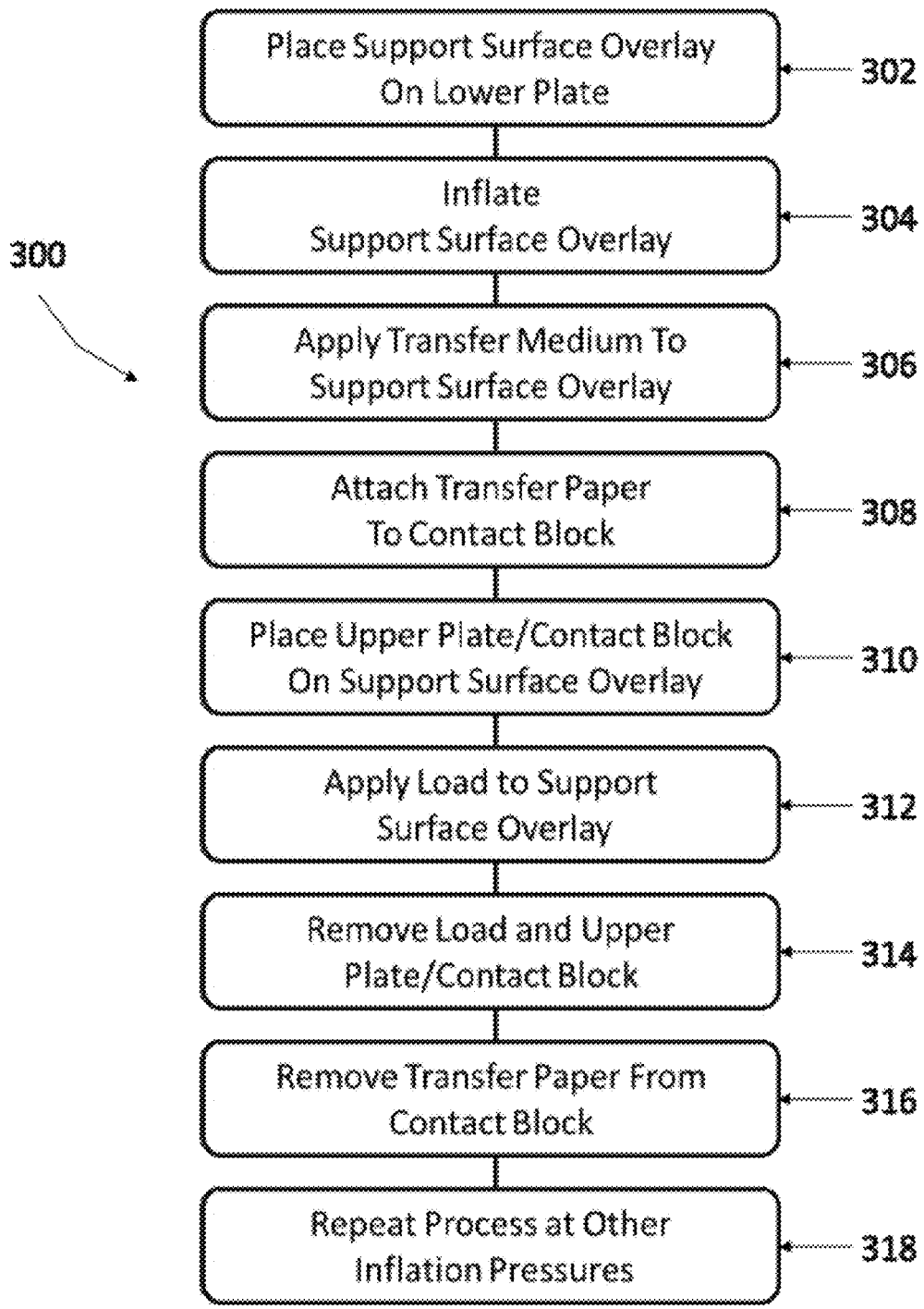

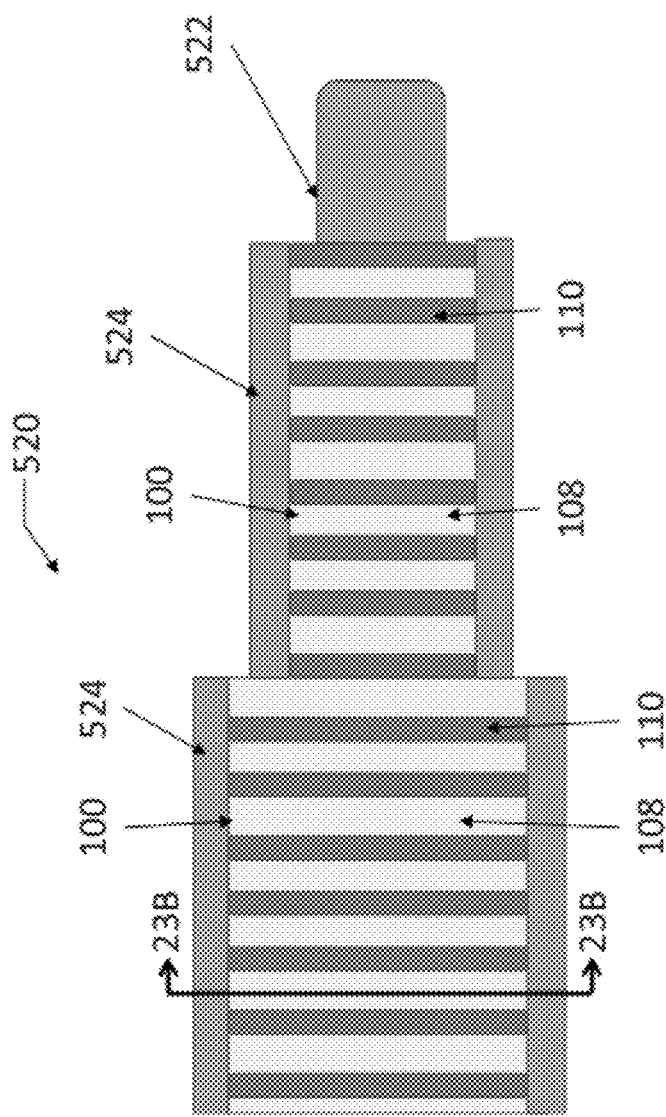
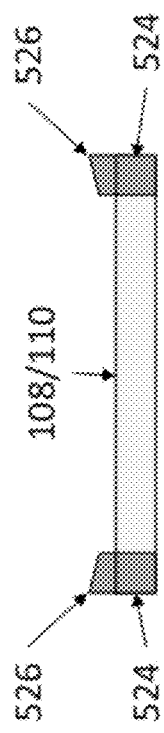
FIG. 23A
FIG. 23B

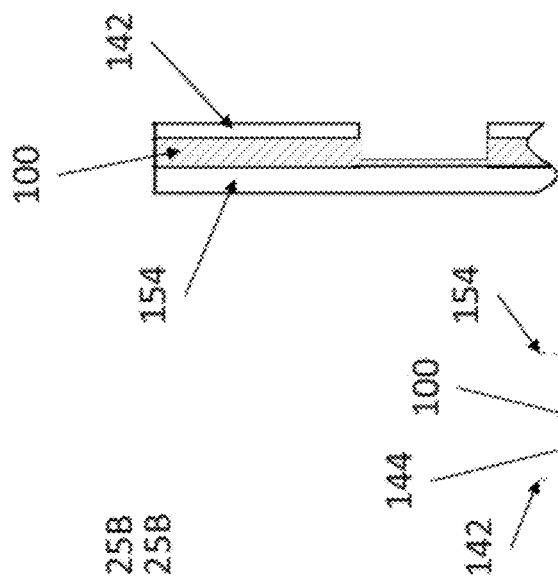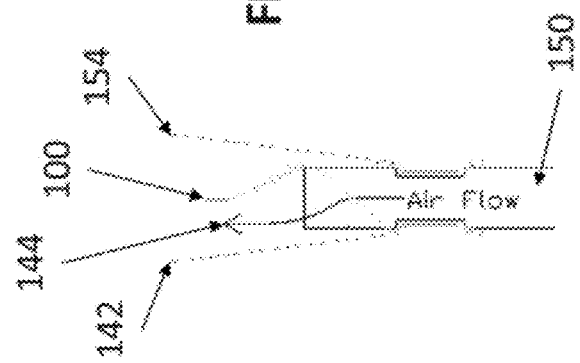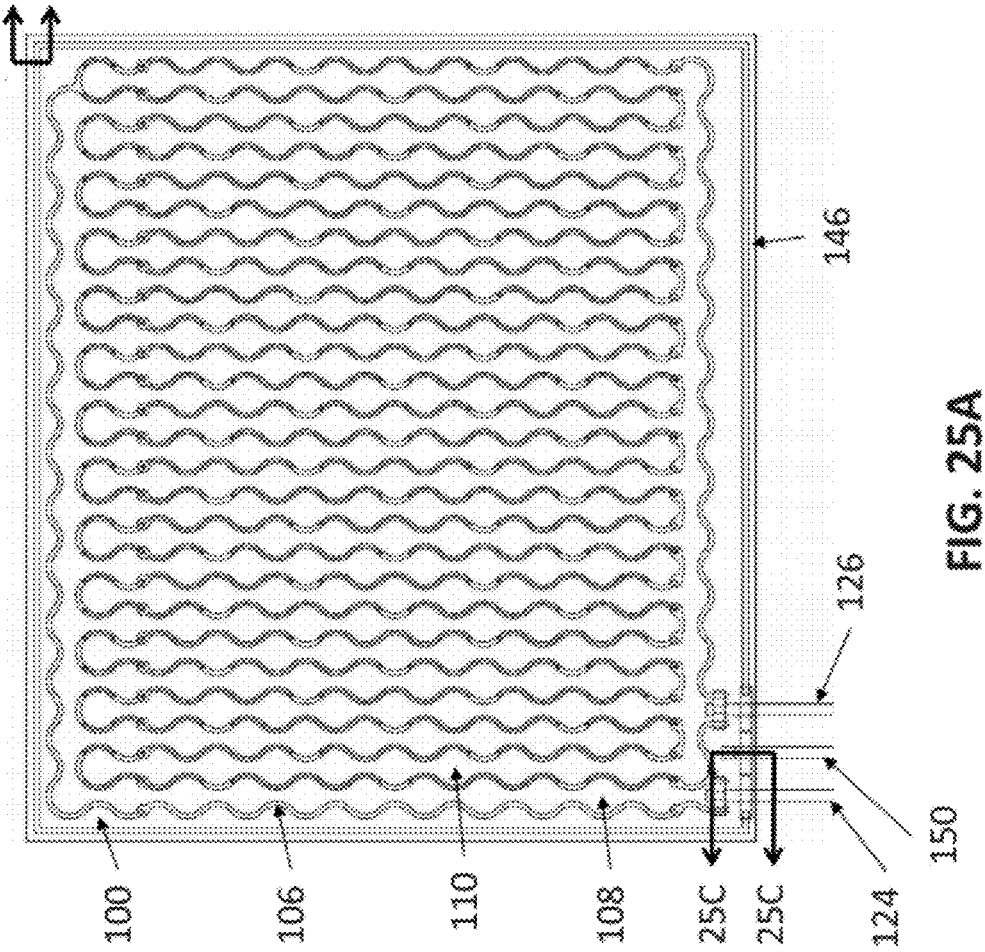

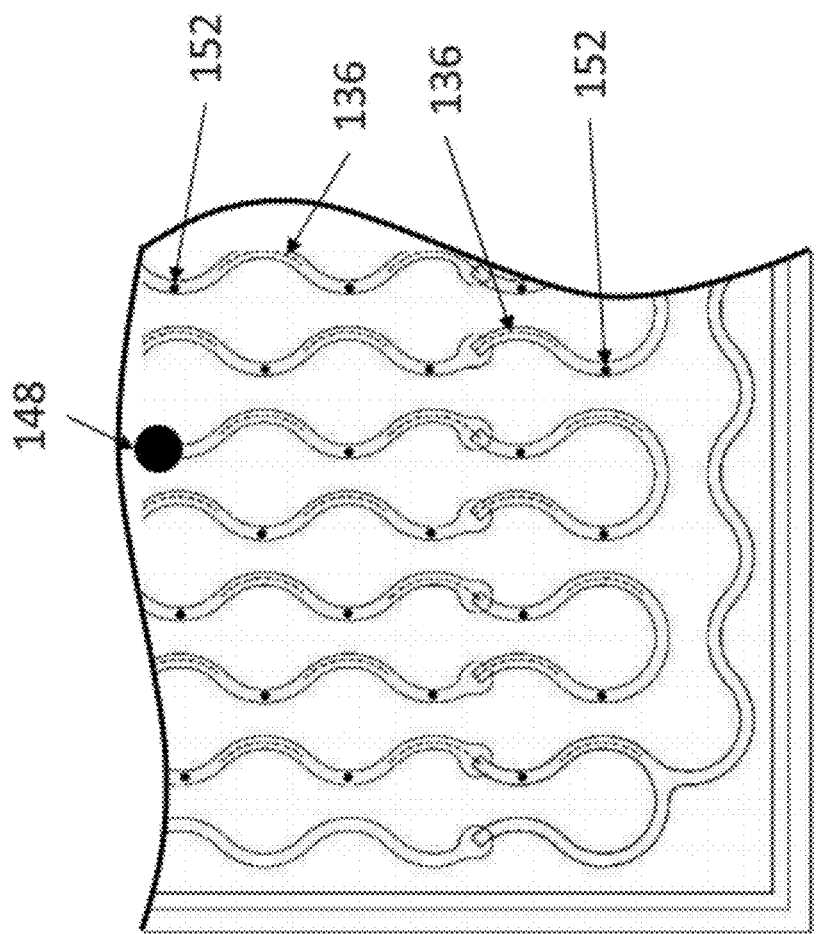

SUPPORT APPARATUS, SYSTEM AND METHOD

CROSS-REFERENCE TO RELATED APPLICATIONS

The present application claims priority to U.S. Provisional Application Ser. No. 61/390,016, filed Oct. 5, 2010, and U.S. Provisional Application Ser. No. 61/535,294, filed Sep. 15, 2011, the disclosures of which are hereby incorporated by reference in their entireties.

BACKGROUND OF THE INVENTION

1. The Technical Field

The present invention is directed to a therapeutic support apparatus, system and method that may be used for mitigating the formation of and/or assisting in the treatment of decubitus ulcers (also sometimes referred to as "pressure ulcers").

2. The Prior Art

Decubitus ulcers can result from excessive and unrelieved pressure applied to a person's body. For example, decubitus ulcers can result from a person lying on a bed, mattress, pad or other support surface in one position for an extended period of time, during which the interface pressure between the support surface and the user's body exceeds the vascular occlusion threshold. The vascular occlusion threshold is the maximum pressure that may be applied to a person's skin by a supporting surface without cutting off subcutaneous or capillary blood flow in the area of the person's body in contact with the supporting surface. Put another way, subcutaneous blood flow is likely to be cut off in areas of contact between a user and a supporting surface if the pressure applied to the person by the support surface exceeds the vascular occlusion threshold. The vascular occlusion threshold is generally deemed to be about 28-32 mm Hg (about 0.5 psi) but can be lower, particularly in users having low blood pressure.

Excessive and unrelieved heat and moisture about the skin and shear forces applied to the skin also can contribute to the formation of decubitus ulcers. Such shear forces can pinch off blood vessels, particularly perforator vessels perpendicular to the skin, and, therefore, inhibit subcutaneous blood flow.

Traditional methods and apparatus for mitigating the formation of and assisting in the treatment of decubitus ulcers involve distributing the user's weight over a relatively large area (typically as large an area as possible) of a support surface so that the interface pressure between the user's body and the support surface generally remains below the vascular occlusion threshold (such techniques sometimes are referred to as "redistribution"). Such methods may further involve alternating areas of the support surface over which the user's weight is distributed.

For example, redistribution techniques sometimes involve the use of relatively thick air mattresses having two alternately inflatable compartments that are operated at low internal pressures (typically 0.5-1.0 psi or less). Operation at such low pressures allows the user's body weight to be distributed over a relatively large area such that a relatively low interface pressure may be realized. One approach uses an air mattress having two alternately inflatable compartments, each defining a plurality of relatively large, generally circular air cells operated at pressures of about 25 mm Hg (about 0.5 psi) that distribute the user's weight over a relatively large surface area. The air cells are about 5 inches in diameter, and the air mattress has a thickness of about 2.5 inches or greater when inflated. Another approach involves a support pad having smaller, more-closely spaced, and elongated air cells. The air cells and fluid channels connecting them are formed into the surface of the pad.

Redistribution techniques have not proven to be entirely satisfactory. Such techniques do not necessarily provide for maintenance of adequate subcutaneous blood flow or adequate relief from shear and environmental effects.

SUMMARY OF THE DISCLOSURE

This disclosure describes exemplary support surface overlays and other apparatus, systems, and methods for supporting a patient or other user and controlling the microclimate about the user in a manner that may mitigate the formation and/or assist in the treatment of pressure ulcers. The support surface overlays depart significantly from support apparatus using redistribution techniques in that they selectively impart relatively high interface pressure to relatively small areas of a user's body. Indeed, the support surface overlays may selectively impart upon the user interface pressures substantially exceeding the vascular occlusion pressure at certain points of contact between the apparatus and the user. At the same time, however, the support surface overlays may impart interface pressures substantially lower than the vascular occlusion pressure (or no interface pressure at all) at other areas of the user's body, for example, areas adjacent to such points of contact or areas corresponding to interstices between such points of contact. As such, subcutaneous blood flow about such points of contact (sometimes referred to herein as "interstitial blood flow") may actually be improved over support apparatus involving generally lower interface pressures at the points of contact. Also, the contact points may closely match the relative spacing of the skin's perpendicular perforator vessels and thereby may be less likely to pinch off those vessels as a result of skin shear as compared to apparatus having larger cell sizes and/or spacing, which can involve substantial skin shear due to envelopment or hammock effects, as would be understood by one skilled in the art.

An illustrative support surface overlay takes the form of a bladder having one or more inflatable compartments. Each inflatable compartment defines one or more relatively small inflatable cells. The inflatable cells of a given compartment and/or the support surface overlay as a whole may be arranged in a matrix of rows and columns or in another geometric form, for example, concentric circles or interwoven spirals. When an inflatable compartment is inflated with a fluid (for example, air, another gas or a liquid), at least some of the inflatable cells also become inflated so as to form contact nodes that impart focused pressure at discrete points on a user's body. These contact nodes also define interstices there between, at least some of which interstices may provide the user's body with partial or complete relief from contact pressure. Such interstices also may form channels allowing for flow of air or another fluid there through. Such fluid flow can be used to control or condition the temperature and/or humidity at the interface between the support surface overlay and a user disposed thereon.

In embodiments including more than one inflatable compartment, the individual inflatable compartments can be independently inflated. Also, the inflatable cells of each inflatable compartment may be located adjacent or between the inflatable cells of one or more other inflatable compartments. In such embodiment, the inflatable cells and interstices may be arranged in rows or in other manners, for example, in sinuous shapes.

Nipple-like protrusions can be provided in connection with one or more of the inflatable cells. Where provided, the nipple-like protrusions can further focus pressure at discrete points on a user's body. The nipple-like protrusions can be formed into the support surface overlay so that they are inflated with their respective inflatable cells or they can be joined to the support surface overlay as a sealed bubble filled with air, another fluid, a gel, or a solid material. They also could be formed of a solid material attached to the support surface overlay or integrally formed with the support surface overlay. Alternatively, they can be provided in a flexible overlay sheet formed separately from and placed over or fixed to the support surface overlay.

In operation, a user can sit or lie on the support surface overlay, and the fluid pressure in the one or more inflatable compartments can be adjusted so that the inflatable cells form corresponding contact nodes and interstices there between. The contact nodes may focus pressure at certain points or portions of the user's body, while the interstices may allow for relief of pressure from other points or portions of the user's body. The internal inflatable compartment pressure that might be required to achieve the desired effect may be a function of the size of the inflatable cells, the number of inflatable cells in contact with a user, the spacing of the inflatable cells from each other, and the weight of the user. Other factors may be relevant, as well. The internal inflatable compartment pressure might range from 2 psi or less to 15 psi or more depending on the application and the design and dimensions of the support surface overlay and elements thereof.

Also, the pressure in the inflatable compartment(s) can be varied in one or more patterns in a manner that massages the user and further promotes localized capillary and lymphatic blood flow. For example, in a support surface overlay having only one inflatable compartment, the inflatable compartment could be sequentially inflated and deflated. In a support surface overlay having two inflatable compartments, both compartments could be simultaneously inflated or deflated, or the two compartments could be inflated and deflated in an alternating manner, so that the respective contact nodes of the two compartments alternately support the user's body at different locations, thereby changing the locations of the user's body where subcutaneous blood flow might be inhibited due to contact with the contact nodes.

The level of control of pressure relief and massaging could be increased by increasing the number of inflatable compartments used in a particular support surface overlay and/or increasing the number of support surface overlays used in a particular application and/or by modifying the manner in which the control mechanisms inflate and deflate the compartments.

The support surface overlay may be used in place of a mattress, pillow or pad. Alternatively, it may be used on top of a mattress, pillow, pad or any other pressure redistribution surface. It may also be used upon or otherwise in connection with chairs, vehicle seats, wheelchairs, and other support surfaces upon which a patient might be disposed for long periods of time.

The support surface overlay also can be placed on an operating table or imaging device, for example, an x-ray machine, fluoroscope, CT scanner, MRI apparatus, etc., to provide pressure relief to a user lying thereon. Preferably, the bladder (and nipple-like protrusions, if provided) appear transparent to such imaging devices.

The support surface overlay can be included as part of a system including control mechanisms, auxiliary support devices, underlying support surfaces, and/or other elements.

BRIEF DESCRIPTION OF THE DRAWINGS

The attached drawings are part of the specification and illustrate certain exemplary embodiments of the present invention as well as their component parts. The components in the drawings are not necessarily to scale, emphasis instead being placed upon illustrating the principles of the present invention.

FIG. 1 is a top plan view of an exemplary support surface overlay according to the present invention;

FIG. 2 is a section view of an inflatable region of the support surface overlay of FIG. 1;

FIG. 3 is a top plan view of the support surface overlay of FIG. 1 with nipple-like protrusions provided thereon;

FIGS. 4A and 4B are section views of an inflatable region of different embodiments of the support surface overlay of FIG. 3;

FIG. 10 is a flow chart illustrating a test procedure;

FIGS. 23A and 23B are plan and section views of an exemplary pad including an exemplary support surface overlay;

FIG. 25A is a top plan view of a support surface overlay including means for providing climate control proximate an upper side thereof;

FIG. 25B is a partial section view of the support surface overlay of FIG. 25A;

FIG. 25C is another partial section view of the support surface overlay of FIG. 25A;

FIG. 25D is a top plan view of a portion of the support surface overlay of FIG. 25A;

DETAILED DESCRIPTION OF THE DRAWINGS

Figure 5:
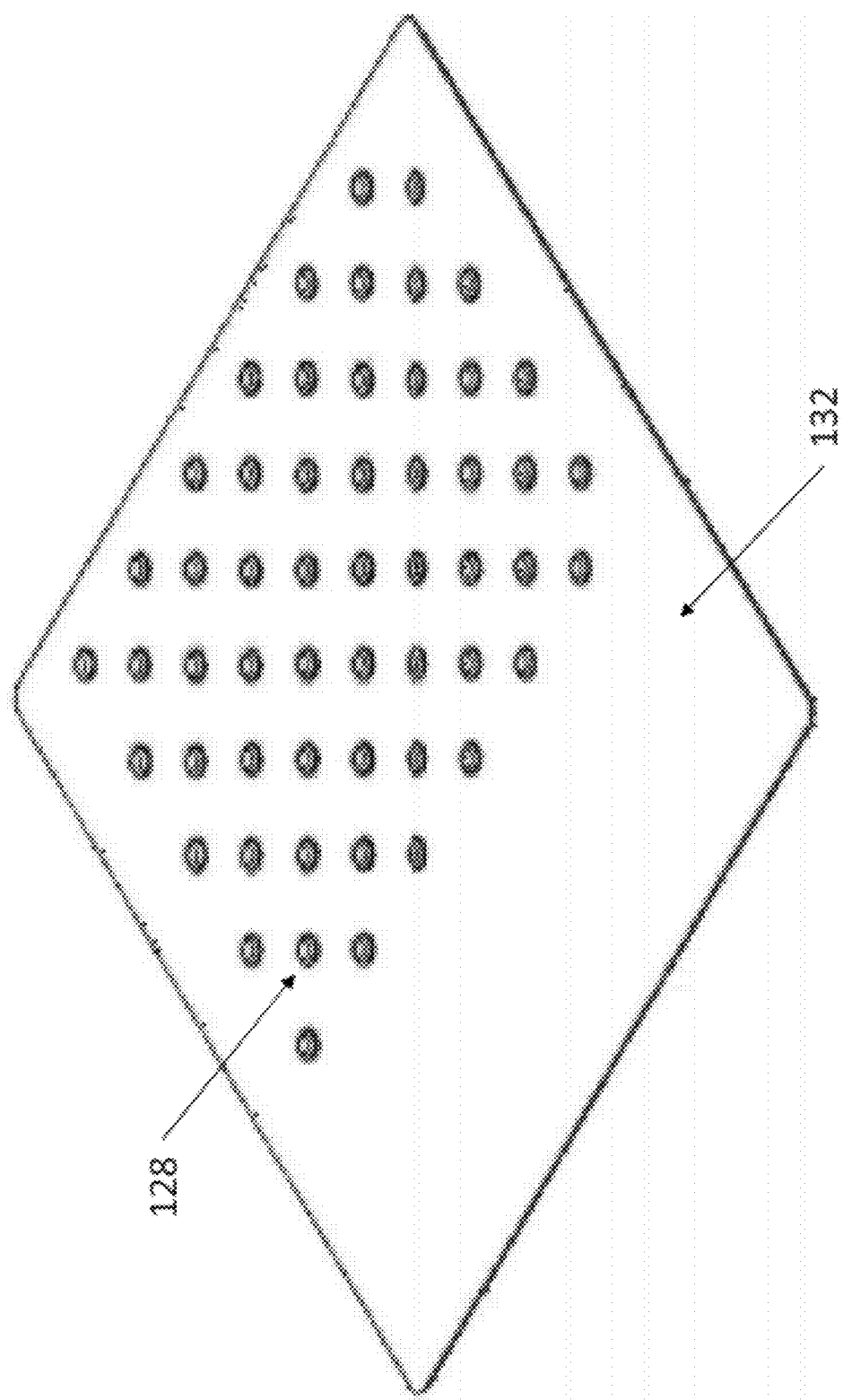
FIG. 5 is an isometric view of a flexible overlay sheet according to a non-limiting embodiment of the present invention.

The drawings illustrate exemplary embodiments of support surface overlays, control systems for operating the support surface overlays, and other elements that may be incorporated into or otherwise used with the support surface overlays.

1. Support Surface Overlays

FIGS. 1 and 2 illustrate a support surface overlay 100 in the form of a bladder formed from a first sheet 102 (sometimes referred to herein as "upper" sheet 102) and a second sheet 104 (sometimes referred to herein as "lower" sheet 104) of flexible material. (References to "upper" and "lower" and to directions and orientations herein generally are for the purpose of illustration and should not be deemed to limit the manner in which devices or components discussed herein may be oriented.) Upper sheet 102 and lower sheet 104 may be substantially flat or planar or otherwise form a substantially continuous surface, at least at points where upper sheet 102 and lower sheet 104 are joined to each other. (Upper sheet 102 and/or lower sheet 104 may include discontinuities or formed elements at points away from such junctions, as discussed further below.) Upper sheet 102 and lower sheet 104 may be made of any suitable material, as would be recognized by one skilled in the art. Preferably, but not necessarily, such material resists taking on electrical charge so as to not become a potential source of electrostatic discharge. In one embodiment, upper sheet 102 and lower sheet 104 may be made of Dow (or Lubrizol) Pellethane 2103-90AE having a nominal thickness of about 0.014 in.

Upper sheet 102 is fused to lower sheet 104 at predetermined locations using an RF welding technique or any other technique suitable for joining upper sheet 102 to lower sheet 104 in a generally fluid-tight manner, thereby forming one or more seams 106. Each seam 106 may include a single fusion or weld line or two or more spaced-apart fusion or weld lines. In embodiments where a seam 106 includes multiple fusion or weld lines, such fusion or weld lines preferably are arranged such that they generally conform to each other. Support surface overlay 100 may be substantially flat or planar when deflated. Preferably, upper and lower sheets 102, 104 and seams 106 appear transparent to a medical imaging device.

Seams 106 divide support surface overlay 100 into first and second independent and separately inflatable compartments 108 and 110. In the FIG. 1 embodiment, first inflatable compartment 108 includes a first compartment manifold 112 and a number of first compartment rows 114 extending therefrom. Similarly, second inflatable compartment 110 includes a second compartment manifold 116 and a number of second compartment rows 118 extending therefrom. First compartment rows 114 are shown as generally adjacent and interspersed with second compartment rows 118. In other embodiments, first and second inflatable compartments 108, 110 can be arranged in other ways.

Adjacent first compartment rows 114 and second compartment rows 118 are shown as sharing a common seam 106 having a single fusion or weld line. This design allows for efficient manufacturing because a single RF weld can be used to form inflatable multiple compartments. It also allows for a relatively high density of first and second compartment rows 114, 118 in a given footprint. In other embodiments, first inflatable compartment 108 and second inflatable compartment 110 need not share a common seam 106. In further embodiments, second inflatable compartment 110 can be omitted. In such embodiments, seams 106 could simply define the boundary between first inflatable compartment 108 and other portions of support surface overlay 100.

In FIG. 1, first compartment 108 is shown as including four first compartment rows 114, and second compartment 110 is shown as including four second compartment rows 118. In other embodiments, either or both of first compartment 108 and second compartment 110 could include as many or as few (as few as one) rows 114, 118 as may be practical. First compartment manifold 112 and second compartment manifold 116 are shown as being aligned with the sides of support surface overlay 100, and first compartment rows 114 and second compartment rows 118 are shown as being aligned with the sides of support surface overlay 100 and oriented at right angles to manifolds 112 and 116, respectively. Manifolds 112, 116 and rows 114, 118 could be oriented in other manners, as well.

In FIG. 1, support surface overlay 100 is shown as having a generally square overall shape. In other embodiments, support surface overlay 100 could have other rectangular, non-rectangular or curvilinear overall shapes. For example, support surface overlay 100 could have a generally elongated shape. In such an embodiment, rows 114, 118 could extend in a direction corresponding to the longer (length) or shorter (width) dimension of support surface overlay 100. In another embodiment, support surface overlay 100 could have a circular shape. In such an embodiment, first and second compartments 108, 110 could be arranged, for example, in concentric circles, spirals, or in another two-dimension or three-dimensional manner, rather than in rows. In such embodiments, manifolds 112, 116 could be omitted.

Seams 106 are shaped to define a number of inflatable cells 120 in fluid communication with each other in each of first compartment rows 114 and second compartment rows 118, for example, as shown in FIG. 1. When inflated, inflatable cells 120 form corresponding contact nodes 122 and define interstices between neighboring contact nodes, as shown, for example, in FIG. 2 and as discussed further below. Seams 106 are shown as being sinusoidal or generally sinuous in shape, such that inflatable cells 120 have a generally circular shape. As such, when inflated, inflatable cells 120 take on a generally spherical shape, thereby forming contact nodes 122, as shown in FIG. 2. The portion of inflatable compartments 108 and 110 joining adjacent inflatable cells 120 may preclude inflatable cells 120 and contact nodes 122 from becoming perfectly spherical, as would be recognized by one skilled in the art. Indeed, in the FIG. 1 embodiment, the shape of contact nodes 122 may be generally football-like at relatively low inflation pressures and become more spherical at increased inflation pressures.

In other embodiments, seams 106 could have other repeating or non-repeating shapes, yielding inflatable cells 120 having corresponding shapes. For example, seams 106 could be shaped in the form of: repeating ramped waves that, for example, ramp up, level off, ramp down and level off, so as to form inflatable cells 120 having a generally hexagonal shape; repeating square waves forming inflatable cells 120 having a generally square shape; repeating saw tooth shapes forming inflatable cells 120 having a generally diamond-like shape; or repeating saw tooth shapes alternating with generally linear shapes thereby forming inflatable cells 120 having a generally triangular shape. In such embodiments, contact nodes 122 take on corresponding shapes when inflatable compartments 108, 110 (including inflatable cells 120) are inflated.

A first fluid conduit 124 can be provided in fluid communication with the interior region of first compartment 108 and a second fluid conduit 126 can be provided in fluid communication with the interior region of second compartment 110 so that the compartments can be selectively charged with and emptied of a fluid (for example, air or another gas or a liquid). Fluid conduits 124, 126 can be made of a plastic material or another suitable material. The ends of fluid conduits 124, 126 attached to support surface overlay 100 can be disposed between upper and lower sheets 102, 104. Alternatively, the ends of fluid conduits 124, 126 attached to support surface overlay 100 could be disposed through corresponding perforations in either of upper and lower sheets 102, 104. In either event, such ends could be RF welded or otherwise attached to upper and/or lower sheet 102, 104 in a manner allowing for a substantially fluid tight connection there between.

In some embodiments, support surface overlay 100 may be provided with nipple-like protrusions 128 at one or more inflatable cells 120. FIG. 3 illustrates one such embodiment as viewed from above. As illustrated in FIG. 4A, nipple-like protrusions 128 can be formed as part of upper sheet 102 of support surface overlay 100 and inflated along with the associated inflatable cells 120 when the corresponding inflatable compartment 108, 110 is inflated. Alternatively, as illustrated in FIG. 4B, nipple-like protrusions 128 can be provided as a third layer 130 attached to upper sheet 102 of support surface overlay 100 by RF welding or another suitable technique. In such embodiments, air, another fluid, a gel, or a solid material could be captured between upper sheet 102 of support surface overlay 100 and third layer 130 so that nipple-like protrusions 128 maintain their shape even when the corresponding inflatable compartment 108, 110 of support surface overlay 100 is deflated. As another alternative, third layer 130 could be embodied as a solid piece of material attached to upper sheet 102 in a suitable manner. Preferably, nipple-like protrusions 128 and their constituent components appear transparent to a medical imaging device.

Nipple-like protrusions 128 need not be integral with upper sheet 102 of support surface overlay 100, as discussed above. Instead, as illustrated in FIG. 5, nipple-like protrusions 128 may be provided on a separate, flexible overlay sheet 132 that can be disposed on support surface overlay 100 so that nipple-like protrusions 128 are aligned over inflatable cells 120 of first and/or second inflatable compartments 108 and 110. In such embodiments, nipple-like protrusions 128 can be formed by fusing two layers of material and capturing air, another fluid or a gel therebetween in the desired protruding shape in a manner similar to that discussed above in connection with embodiments wherein nipple-like protrusions 128 are integral with upper sheet 102 of support surface overlay 100. Alternatively, nipple-like protrusions 128 and overlay sheet 132 could be integrally formed as a single sheet of material, such as plastic or rubber. Preferably, nipple-like protrusions 128 and overlay sheet 132 are substantially transparent to medical imaging devices. In use, overlay sheet 132 may simply be placed over support surface overlay 100, or overlay sheet 132 may be permanently attached to upper sheet 102 of support surface overlay 100 using RF welding, bonding, or another suitable attachment mechanism.

Figure 26A:
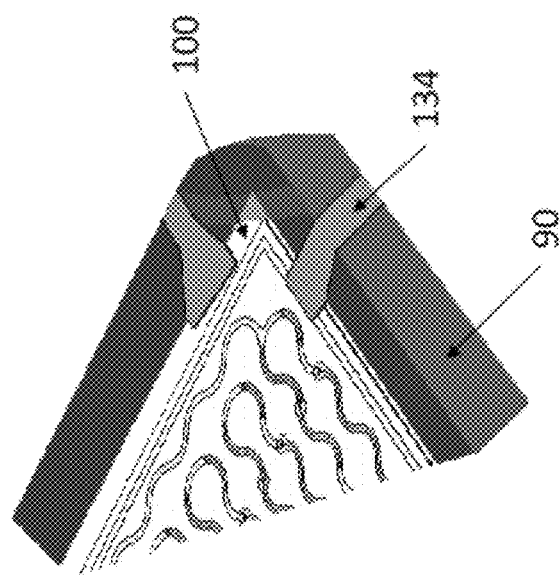
FIG. 26A is a perspective view of a support surface overlay including attachment straps.
Figure 26B:
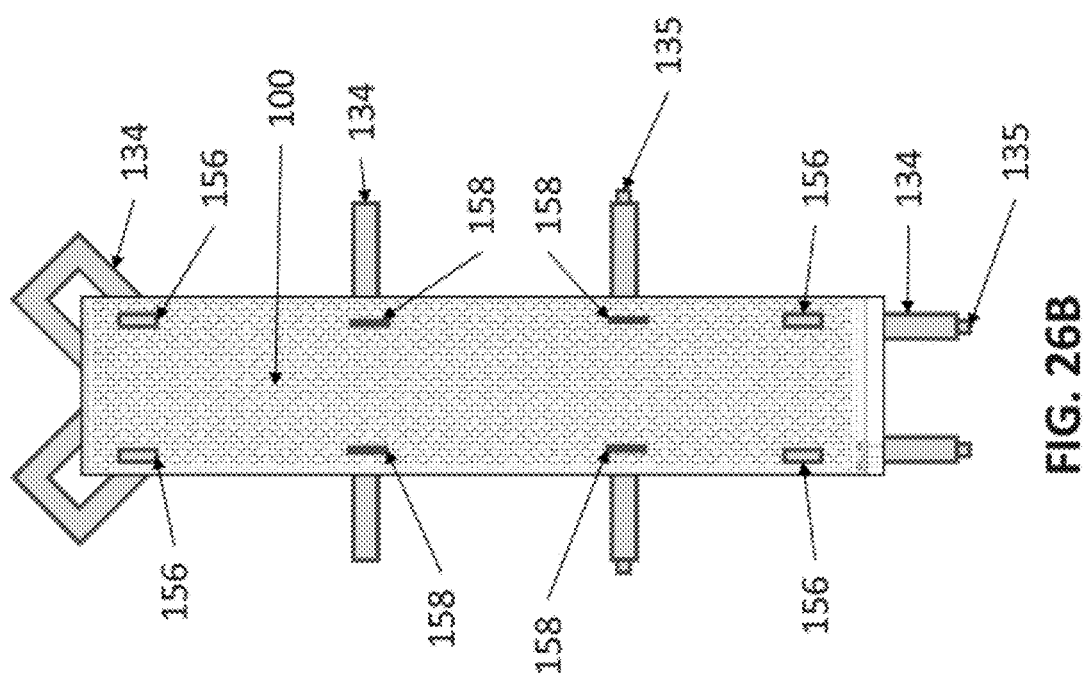
FIG. 26B is a top plan view of a support surface overlay including attachment straps and hand holds.

With reference to FIGS. 1, 26A and 26B, support surface overlay 100 may include one or more straps 134 for attaching support surface overlay 100 to an underlying support surface, for example, a bed or seat. Straps 134 could be made of any suitable material and attached to support surface overlay 100 in any suitable manner. For example, straps 134 or relevant portions thereof could be made of a material compatible with the material of which support surface overlay 100 is made so that straps 134 could be RF welded to support surface overlay 100. Alternatively, support surface overlay 100 could include slots 158 (as shown in FIG. 26B), grommets and/or other apertures (not shown) proximate the perimeter thereof through which straps 134 could be threaded.

Only two straps 134 are illustrated in FIG. 1, extending from corners of support surface overlay 100. In practice, support surface overlay could include more straps 134, as desired, and straps 134 could extend from any portion of support surface overlay 100 including other corners or sides thereof. For example, as shown in FIGS. 26A and 26B, straps 134 could extend from the sides and/or ends of support surface overlay 100. As shown in FIGS. 26A and 26B, straps 134 could be attached to support surface overlay 100 at both ends and configured to hook over the corner of a mattress 90 to secure support surface overlay 100 to the mattress. In such embodiments, at least portions of straps 134 could be made of an elastic material. In other embodiments, straps 134 could include buckles or hook-and-loop fasteners 135 or other adjusting and securing means so that straps 134 can be used to secure support surface overlay 100 to an underlying support surface, for example, mattress 90 or another support surface.

With reference to FIG. 26B, support surface overlay 100 may include hand holds 156 cut into support surface overlay 100 about the periphery thereof, thereby providing means for personnel to securely grip and carry support surface overlay 100 with a user disposed thereon.

The overall length and width of support surface overlay 100 can be selected as desired for a particular application. For example, support surface overlay 100 can be sized to overlie a standard mattress, individual sections of an articulating mattress as might be used in an articulating hospital bed, a catheter table, an MRI table, an operating table, a wheelchair seat, a vehicle seat, another form of seat, the limb-receiving cup of a prosthetic device, another form of support surface for an individual, etc.

Figure 7:
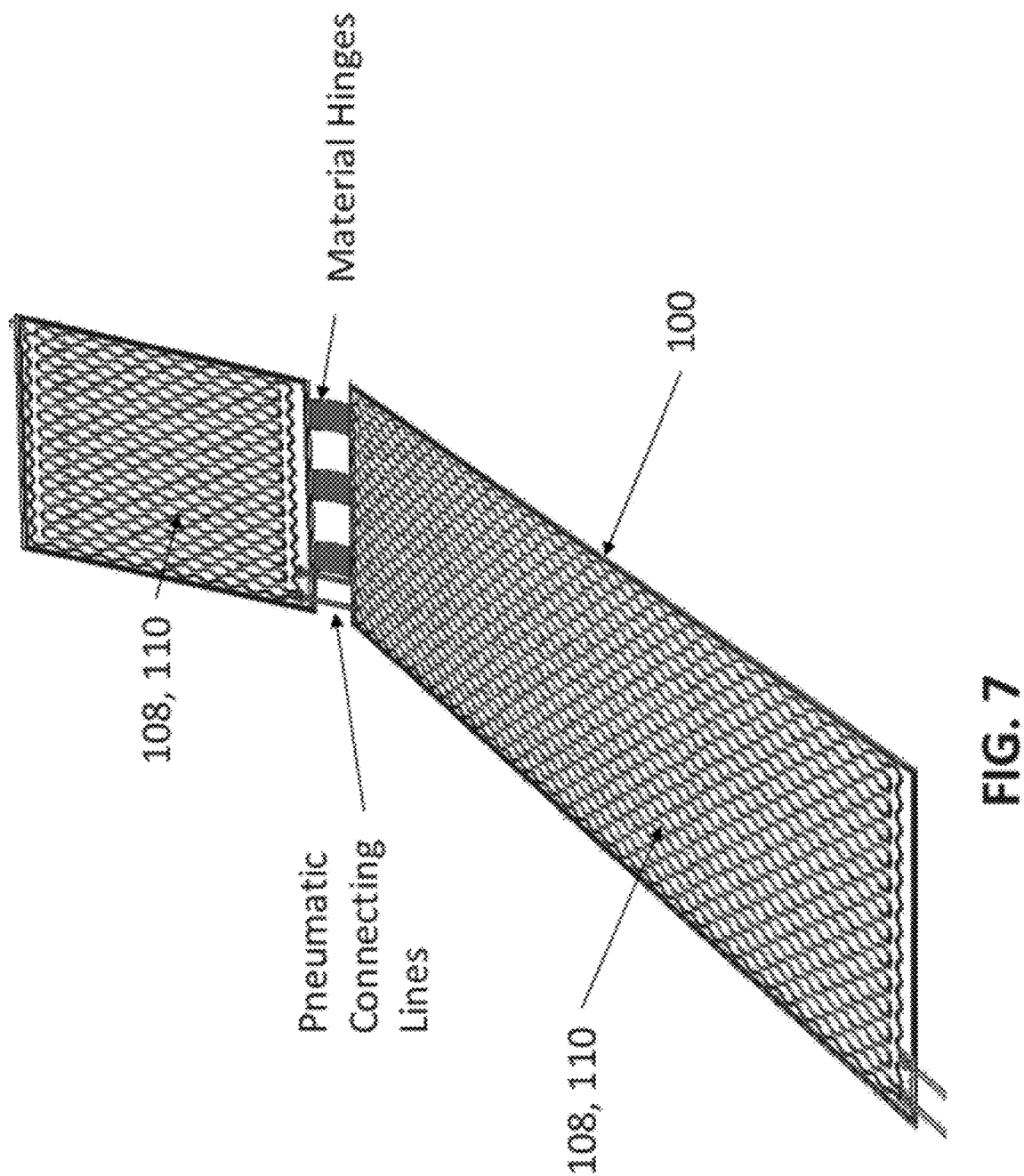
FIG. 7 is a perspective view of an articulating support surface overlay.

As shown in FIG. 7, support surface overlays 100 can include multiple bladder sections, each including separate and distinct first and/or second inflatable compartments 108, 110, can be formed from a single upper sheet 102 and lower sheet 104. Such embodiments enable articulation of upper sheet 102 and lower sheet 104 without pneumatically or hydraulically pinching portions of inflatable compartments within ones of such bladder sections.

Preferably, but not necessarily, support surface overlay 100 is sufficiently flexible so that it may be rolled up for shipping or storage and so that it is "self contouring" to an underlying support surface it might be placed upon, for example, a pressure redistribution surface or any other flat, concave, convex or otherwise contoured surface.

In operation, first inflatable compartment 108 and second inflatable compartment 110 can be selectively and independently inflated and deflated. When either of inflatable compartments 108, 110 is inflated, the inflatable cells 120 of the respective compartment inflate to a generally spherical shape (for example, a compressed spherical shape such as that shown in FIG. 2) and form contact nodes 122 as discussed above. Contact nodes 122 can support a load, for example, a human body. The inflation pressure within inflatable compartments 108, 110 can be selected such that a body supported by support surface overlay 100 rests substantially upon contact nodes 122 and preferably not upon other parts of support surface overlay 100, for example, the interstices between neighboring contact nodes 122. In practice such inflation pressures may range from 1 psi or less to 15 psi or more, depending on the configuration of support surface overlay 100. In this state, the interface pressure between contact nodes 122 and the body supported thereon may substantially exceed the vascular occlusion threshold such that subcutaneous blood flow in areas of the body impinging contact nodes 122 may be substantially inhibited or even cut off. At the same time, however, the interface pressure between other portions of support surface overlay 100, for example, the interstices between neighboring contact nodes 122, and the body supported by contact nodes 122 may be substantially less than the vascular occlusion threshold, such that subcutaneous blood flow in areas of the body overlying the interstices may be preserved or otherwise not substantially inhibited. Indeed, in this state, there may be substantially no contact between the body supported by contact nodes 122 and the interstices between neighboring contact nodes 122, such that the interface pressure in these interstitial regions may be as little as substantially zero. To the extent that there is no contact in the foregoing regions, air or another fluid may be channeled through such regions to, for example, control heat and humidity in such regions, as will be discussed further below.

In operation, first and second inflatable compartments 108, 110 could be alternately inflated and deflated according to one or more predetermined patterns or cycles such that particular contact nodes 122 generally do not impart pressure greater than the vascular occlusion threshold upon the same portions of a body lying on support surface overlay 100 for longer than a predetermined, uninterrupted period of time. For example, first inflatable compartment 108 could be inflated and second inflatable compartment 110 could be deflated for a first predetermined period of time, during which time a first set of contact nodes 122 corresponding to the inflatable cells 102 of first inflatable compartment 108 generally would impart substantial pressure (that might exceed the vascular occlusion threshold) upon corresponding first portions of a body lying on support surface overlay 100. Upon expiration of the foregoing predetermined period of time, second inflatable compartment 110 could become inflated and first inflatable compartment 108 could become deflated for another predetermined period of time, during which time a second set of contact nodes 122 corresponding to the inflatable cells 102 of second inflatable compartment 110 generally would impart substantial pressure (that might exceed the vascular occlusion threshold) upon corresponding second portions of a body lying on support surface overlay 100. The second portions of the body typically would be substantially different from the first portions of the body.

The foregoing cycle could be repeated indefinitely. In some modes of operation, first inflatable compartment 108 could become completely deflated before any substantial inflation of second inflatable compartment 110 and vice versa. In other modes of operation, first inflatable compartment 108 could become deflated while second inflatable compartment 110 becomes inflated and vice versa. In further modes of operation, second inflatable compartment 110 could become completely inflated before first inflatable compartment 108 begins to deflate and vice versa.

In addition to controlling subcutaneous blood flow, operation of support surface overlay 100 as discussed above also can provide massaging action to a user lying thereon. For example, alternately inflating and deflating first and second inflatable compartments 108, 110 can yield an oscillating, wave-like pattern of movement across the inflatable compartments 108, 110 of one or more support surface overlays 100 a user might be disposed upon to massage one or more areas of a user's body and to encourage interstitial blood flow.

The drawings generally illustrate a support surface overlay 100 having two inflatable compartments 108, 110. In other embodiments, a support surface overlay 100 could include more than two inflatable compartments 108, 110 to enable increased complexity of the patterns of movement of inflatable cells 120 that can be created by inflating and deflating the individual inflatable compartments of support surface overlay 100. Indeed, each inflatable cell 120 of support surface overlay 100 could be embodied as a separate and distinct inflatable compartment. In further embodiments, a support surface overlay 100 could include a single inflatable compartment. In some embodiments, support surface overlay 100 could include one or more permanently filled inflatable compartments similar to one or more of the inflatable compartments described herein. In such embodiments, the permanently filled compartments preferably would be filled with a fluid, for example, a silicone hydraulic fluid, that would not permeate upper and lower sheets 102, 104.

A support surface overlay 100 dimensioned so that it satisfies one or more of Criteria A-D set forth below may provide for the foregoing support characteristics (sometimes referred to herein as "Dabir effects"), that is, relatively high local interface pressure between contact nodes 122 and portions of a user's body supported thereon, and relatively low or no interface pressure between interstices defined by contact nodes 122 and a user supported thereon. With reference to FIG. 2, relevant dimensions may include the maximum thickness "t" of any of inflatable cells 120 of support surface overlay 100 when inflated and free of any substantial external load. With reference to FIG. 1, relevant dimensions may also include the nominal diameter "d" of inflatable cells 120 (or other relevant dimension where inflatable cells 120 are not generally circular), the spacing "h" between neighboring inflatable cells 120 within a given inflatable row 114, 118 of first or second inflatable compartment 108, 110 (sometimes referred to herein as "horizontal spacing" or "horizontal pitch"), and the spacing "v" between inflatable cells 102 within a given "column" of inflatable rows 114, 118 (sometimes referred to herein as "vertical spacing" or "vertical pitch"). (As used in this context, the terms "horizontal" and "vertical" refer to orientation relative to rows of inflatable cells 120 as set forth above.) In embodiments wherein inflatable cells 120 are not arranged in columns substantially normal to the rows, the spacing "v" could be measured from a first contact node located in a first row to a second contact node located in a second row that is nearest a line normal to the first row and passing through the first contact node. The spacing between inflatable cells 120 typically is measured from centroid to centroid of the corresponding contact nodes, with inflatable cells 120 inflated, unless otherwise noted. A support surface overlay 100 not satisfying any of Criteria A-D might nevertheless provide Dabir effects, and other criteria may exist which may define whether a support surface overlay 100 is likely to provide Dabir effects.

Criterion A—Bladder Thickness

Figure 31:
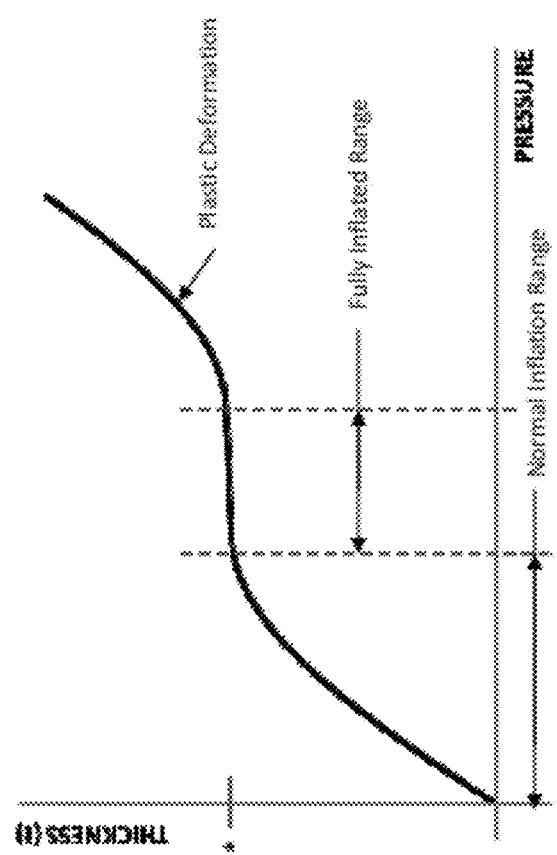
FIG. 31 is a graph showing how the thickness of a support surface overlay may vary with varying pressure.

A support surface overlay 100 with inflatable cells 120 having a maximum nominal thickness t, when fully inflated and free of external loads, of no more than about 2.0 inches may provide the Dabir effect. As used in this context, the term "fully inflated" means inflated to a pressure insufficient to cause plastic deformation of inflatable cells 120 or support surface overlay 100 generally and beyond which an increase in pressure results in at most an insignificant increase in thickness of inflatable cells 120, for example, as illustrated in FIG. 31. Support surface overlay 100 thickness t can be measured using any suitable means, as would be recognized by one skilled in the art. Preferably, support surface overlay 100 would have a thickness t of less than two inches, for example, 1.875 inches, 1.75 inches, 1.625 inches, 1.5 inches, 1.375 inches, 1.25 inches, 1.125 inches, 1 inch, 0.875 inch, 0.75 inch, 0.625 inch, 0.5 inch, 0.375 inch, 0.25 inch, 0.125 inch or any other thickness less than about 2.0 inches. (Preferably, support surface overlay 100 would be designed in a manner allowing for a relatively thin thickness t, for example one inch or less, so that motion of a user disposed thereon would be minimized upon inflation and deflation of inflatable compartments 108, 110.)

Criterion B—Nodal Density

A support surface overlay 100 having at least one inflatable compartment having a nodal contact density, when fully inflated, of at least two contact node 122 centroids per square decimeter of support surface overlay 100 surface area may provide the Dabir effect. In this context, the term "fully inflated" means inflated to a pressure insufficient to cause plastic deformation of inflatable cells 120 or support surface overlay 100 generally and beyond which an increase in pressure results in at most an insignificant effect on the length or width of support surface overlay 100 in the area in which the nodal contact density is being measured, for example, as illustrated in FIG. 31. Preferably, support surface overlay 100 would have a nodal contact density of from three to thirty or more contact nodes per square decimeter. Nodal density can be determined by ascertaining the maximum number of contact nodes 122 that can fit within a 10 cm×10 cm area of the surface of support surface overlay 100. For example, nodal density can be determined by fitting a mask having a 10 cm×10 cm opening over support surface overlay 100 and ascertaining the maximum number of contact node 122 centroids that can be made to fit within the opening with support surface overlay 100 fully inflated. Nodal density also could be determined by fitting a mask having a 10 cm×10 cm opening over a transfer paper removed from contact block 206 at step 316 of the test procedure described below in connection with Criteria C and D and determining the maximum number of contact node 122 centroids as may be ascertained from marks imprinted by contact nodes 122 that can be made to fit within the opening with the transfer paper fully inflated.

Criterion C—Nodal Contact Area Density

A support surface overlay 100 dimensioned so that inflatable cells 120, when inflated to a predetermined internal pressure, are capable of supporting a test surface having a predetermined surface area bearing a predetermined load such that less than 75% of the test surface is in contact with contact nodes 122 (and, therefore, at least 25% of the test surface is not in contact with contact nodes 122) should provide the Dabir effect. Preferably, support surface overlay 100 would be dimensioned such that substantially less than 75% is in contact with contact nodes 122 (and, therefore, substantially more than 25% of the test surface is not in contact with contact nodes 122) under such conditions. For example, support surface overlay 100 preferably would be dimensioned such that at least 25%-85% or more of the test surface is not in contact with contact nodes 122 under such conditions. The percentage of contact and non-contact can be determined by any suitable means, for example, using pressure mapping equipment or by analysis of transfer patterns obtained using the test fixture and methodology described below.

Criterion D—Nodal Linear Non-Contact Pattern

A support surface overlay 100 dimensioned so that inflatable cells 120, when inflated to a predetermined internal pressure, are capable of supporting a test surface having a predetermined surface area bearing a predetermined load such that at least 25% of the test surface corresponding to a line substantially normal to a row of inflatable cells 120 and connecting the centroid of an inflatable cell 120 of such row with the centroid of the nearest inflatable cell 120 of another such row falling on such line (for example, a line connecting the inflatable cells 120 shown in FIG. 1 as defining the endpoints of the dimension "v") is not in contact with support surface overlay 100 and less than 75% of the test surface corresponding to that line is contact with support surface overlay 100. In embodiments wherein inflatable cells 120 of neighboring rows are not arranged in columns substantially normal to the rows, the "v" dimension could be measured as discussed above.

Preferably, support surface overlay 100 would be dimensioned so that a substantially greater portion of the test surface corresponding to that line is not in contact with contact nodes 122 under such conditions. For example, bladder 100 preferably would be dimensioned such that at least 25%-85% or more of the test surface corresponding to that line is not in contact with contact nodes 122 under such conditions. The percentage of contact and non-contact can be determined by any suitable means, for example, using pressure mapping equipment or by analysis of transfer patterns obtained using the test fixture and methodology described below. If using the test fixture and methodology described below, it may be desirable to obtain and average the foregoing measurements from the contact patterns associated with three or more pairs of contact nodes.

Percentage of linear contact may be expressed as

% contact=$[A+(C-B)+D]/C*100$ (Equation 1)

and percentage of linear non-contact may be expressed as

Figure 32:
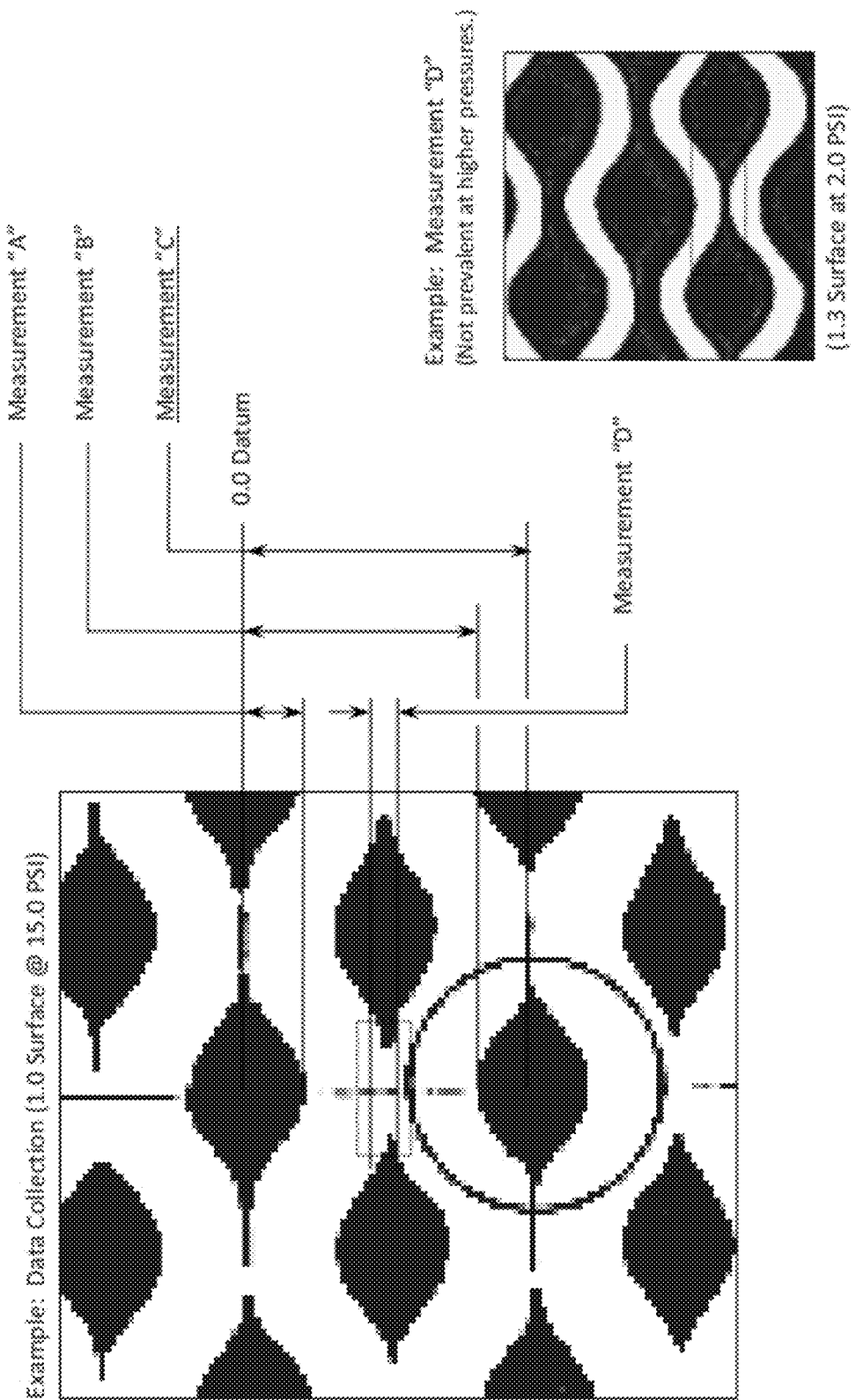
FIG. 32 is a representation of test data as may be obtained using a particular test methodology.

% non-contact=$[B-A-D]/C*100$ (Equation 2)

where A=the center-to-edge distance of a given contact node 122, B=the distance between the center of a given contact node and the edge of a neighboring contact node, C=the center-to-center distance between neighboring contact nodes, and D=the width of any line of contact between horizontally neighboring contact nodes. Dimensions A-D are illustrated in FIG. 32.

Alternatively, % linear non-contact could be determined between any or all pairs of contact nodes 122 that may be connected by a line drawn from centroid-to-centroid of such pair(s) of contact nodes without passing through a third contact node 122 or inflatable cell 120. To the extent that this technique might yield different % non-contact measurements from pair to pair of contact nodes analyzed, Criterion D the analysis should be based on the pair of contact nodes that demonstrates the greatest % of linear non-contact at a given test pressure.

2. Test Fixture and Testing Methodology

Figure 8:
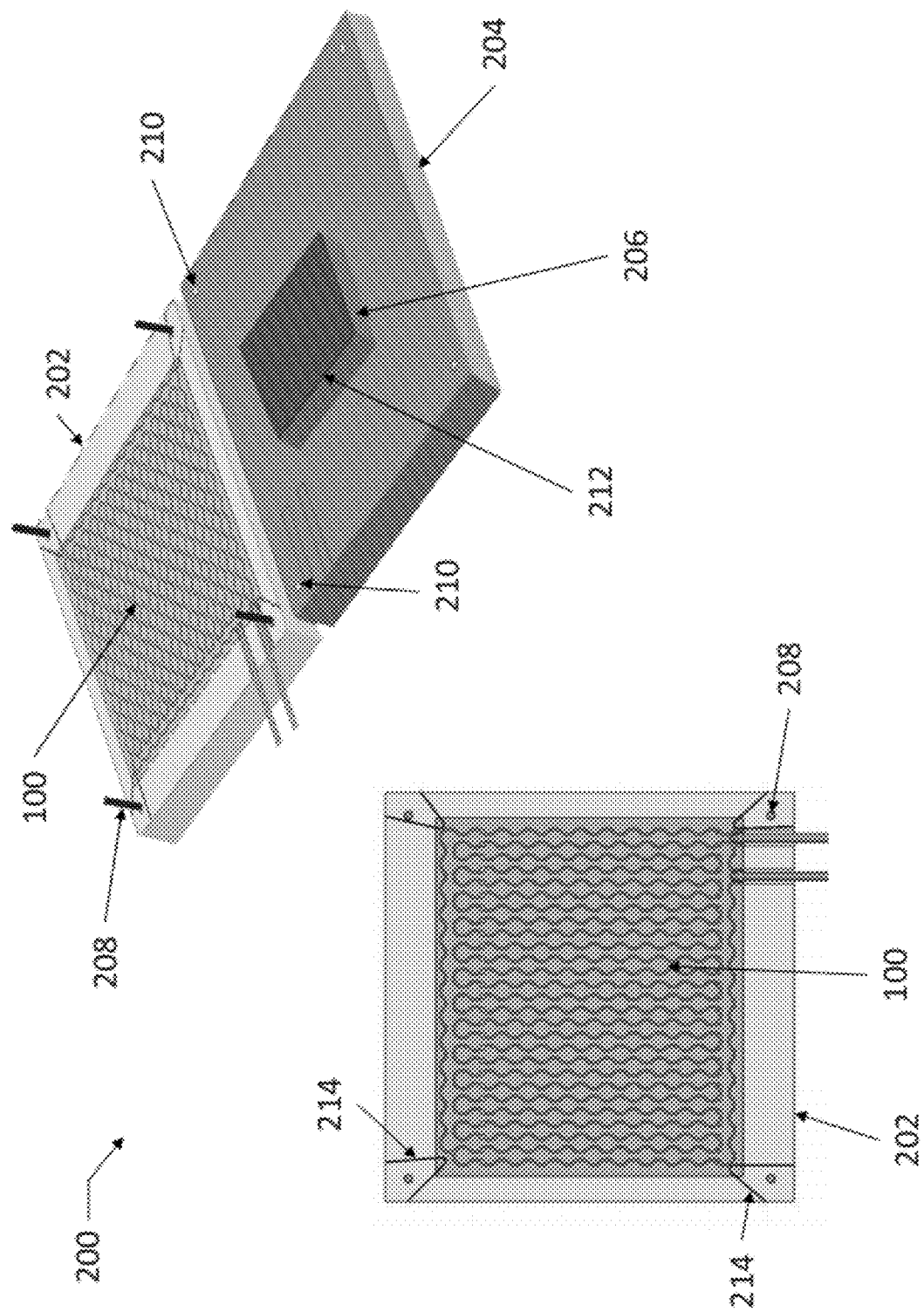
FIGS. 8 and 9 are representations of a test fixture.
Figure 9:
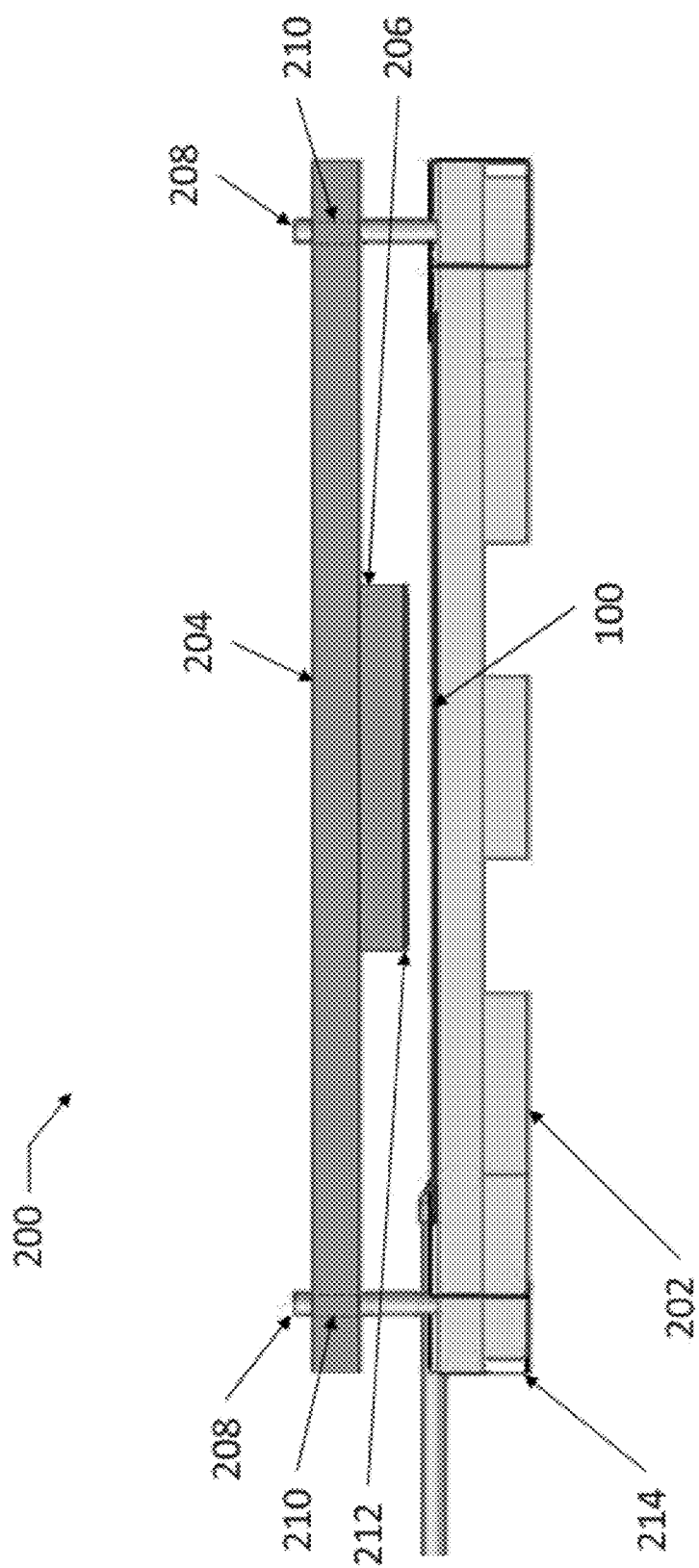

The test fixture and test procedure described below can be used for making the foregoing contact and non-contact area determinations at various inflatable compartment inflation pressures. With reference to FIGS. 8 and 9, test fixture 200 includes a rigid, flat lower plate 202, a rigid, flat upper plate 204, and a contact block 206 attached to the underside of upper plate 204. Contact block 206 may be attached to upper plate 204 using any suitable means such that the upper surface of lower plate 202, lower surface of contact block 206 (the surface of contact block facing away from upper plate 204) and the upper surface of upper plate 204 are substantially parallel when upper plate 204 is placed upon lower plate 202, as discussed further below. Lower plate may include guide pins 208 extending upwardly therefrom, and upper plate 204 may include receiving holes 210 configured to receive guide pins 208.

Lower plate 202 and upper plate 204 may be made of any suitable, rigid material, for example, steel. Contact block 206 similarly may be made of any suitable material, for example, steel or wood. A thin foam layer 212 of substantially uniform thickness optionally may be applied to the surface of contact block facing away from upper plate 204. Foam layer 212 may be made of any suitable closed cell foam material, for example, 0.125-0.25 inches thick. When used, foam layer 212 should cover the entirety of such surface of contact block 206.

The test procedure 300 is illustrated in flow chart form in FIG. 10.

At step 302, support surface overlay 100 is placed on lower plate 202. Preferably, support surface overlay 100 is loosely stretched into position on lower plate 202 so that support surface overlay 100 lies substantially flatly thereon. Support surface overlay 100 may be secured to lower plate 202, if at all, using any suitable means, for example, positioning bands 214 secured to support surface overlay 100 near corners thereof and attached about corners of lower plate 200. When used, positioning bands 214 can further serve to loosely stretch support surface overlay 100 into position as discussed above.

At step 304, inflatable cells 120 of support surface overlay 100 are inflated to a predetermined pressure.

At step 306, a transfer medium, for example, a layer of paint or ink, is applied to the upper surface of support surface overlay 100, that is, the surface of support surface overlay 100 facing away from lower plate 202.

At step 308, a piece of transfer paper or other material for receiving the transfer medium applied to support surface overlay 100 is removably attached to contact block 206 using, for example, tape or another form of removable adhesive, for example, a spray adhesive.

At step 310, upper plate 204 is placed upon support surface overlay 100 so that the transfer paper attached to contact block 206 makes contact with support surface overlay 100. In embodiments wherein lower plate 202 includes guide pins 208 and upper plate 204 includes receiving holes 210, upper plate 204 is placed upon support surface overlay 100 so that receiving holes 210 of upper plate receive guide pins 208 of lower plate 202.

At step 312, a predetermined load is gently applied to support surface overlay 100. The predetermined load includes the weight of upper plate 204 and contact block 206 and may further include an additional load. Such additional load may include weights or another force applied to upper plate 204 in the direction of support surface overlay 100. Such additional load should be applied centrally to upper plate 204 or otherwise in a manner that allows upper plate 204 to evenly apply the load to support surface overlay 100.

At step 314, the load, including upper plate 204, contact block 206, and any additional load, is raised and removed from contact with support surface overlay 100.

At step 316, the transfer paper is removed from contact block 206.

At step 318, the foregoing procedure can be repeated at other predetermined inflatable compartment inflation pressures. Preferably, the procedure is first conducted using relatively high inflatable compartment inflation pressures and then successively lower inflatable compartment inflation pressures but could be conducted in other sequences, as well.

In one embodiment, the surface of contact block 206 that is applied to support surface overlay 100 has dimensions of 6"×6" and contact block 206 and upper plate 204 have a combined weight of about 9.4 pounds. Lower plate 202 preferably has dimensions at least somewhat larger than contact block 206. The transfer paper area is substantially the same as the area of contact block 206 projected against support surface overlay 100. The weight of the transfer paper is negligible. An additional load having a nominal weight of seventy (70) pounds is applied to upper plate 204. Inflatable cells 120 are initially inflated to a pressure of 15 psi. In successive runs, inflatable cells 120 may be inflated to pressures lower than 15 psi in, for example, 1 psi increments.

The data obtained using the foregoing test fixture and methodology can be analyzed to determine whether and at which operating pressures a particular support surface overlay 100 is expected to provide Dabir effects.

The details of the foregoing test fixture and test procedure are exemplary and may vary in other embodiments.

3. Examples

Certain prototype support surface overlays 100, namely, the so-called 1.0 and 1.3 support surface overlays, have been used to develop and/or confirm the foregoing criteria.

The 1.0 support surface overlay is characterized by inflatable cells 120 having a nominal diameter of 0.80 inches, nominal horizontal spacing of 1.29 inches and nominal vertical spacing of 1.24 inches. The 1.0 support surface overly has a nominal thickness t of 0.413 and, therefore, satisfies Criterion A above. The 1.0 support surface overlay has a nodal contact density of 24 nodes per square decimeter and, therefore, satisfies Criterion B above.

In testing performed using the fixture and methodology set forth above, the 1.0 support surface exhibited the % contact area vs. inflation pressure characteristics shown in Table 1 below.

TABLE 1

| Pressure (psi) | % Area Contact |
|---|---|
| 1.5 | 98.75 |
| 3.0 | 63.53 |
| 6.0 | 43.31 |
| 9.0 | 39.23 |
| 12.0 | 34.87 |
| 15.0 | 30.39 |

Figure 12A:
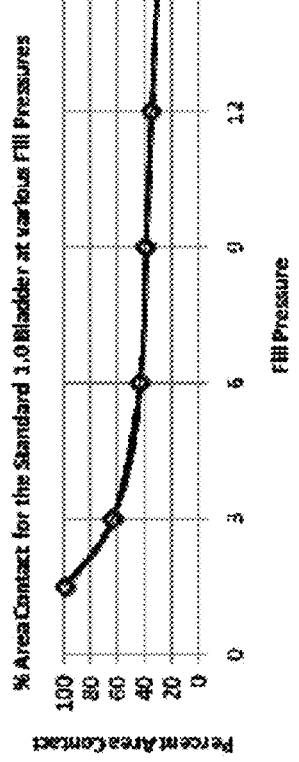
FIG. 12A is a plot of contact area vs. inflation pressure for an exemplary support surface overlay.
Figure 11:
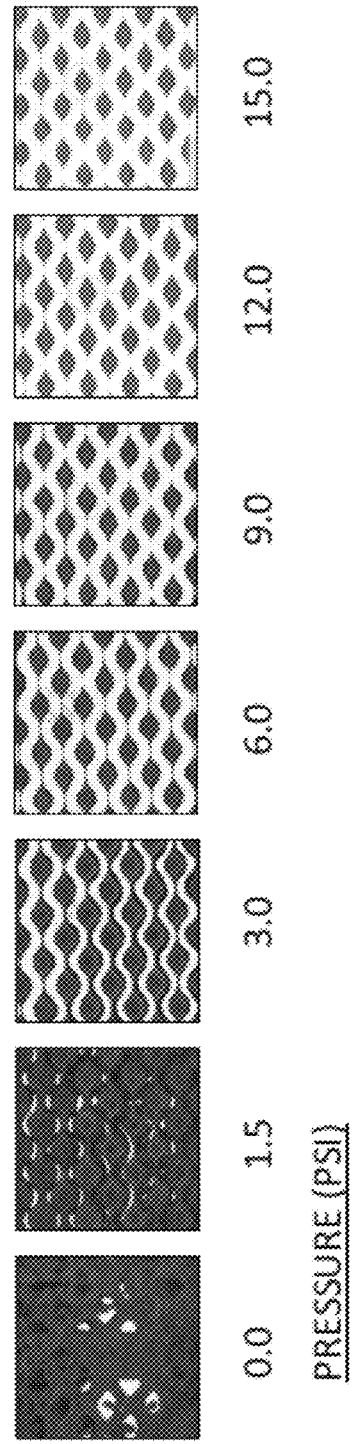
FIG. 11 illustrates contact patterns obtained from tests of an exemplary support surface overlay.

The contact patterns that resulted from the foregoing testing are illustrated in FIG. 11. FIG. 12A is a plot of contact area vs. inflation pressure using the data from Table 1. This data was used to derive Equation 3 defining % contact area (y) as a function of fill pressure (x):

$$y=-0.0013x^5+0.0675x^4-1.3587x^3+13.359x^2-65.401x+171.04 \quad \text{(Equation 3)}$$

at $R^2=1$, where $R^2$ is the coefficient of determination. Solving for fill pressure (x) at contact areas of 50%-75% in 5% increments yields fill pressures as a function of contact area as set forth in Table 2. Table 2 also sets forth an adjusted pressure as a function of % area contact, the adjusted pressure being 20% lower than the pressure obtained from Equation 3. The adjusted pressure is intended to adjust for measurement and other errors that may occur during testing.

TABLE 2

| % Area Contact | Pressure (psi) | Adjusted Pressure (psi) |
| --- | --- | --- |
| 75% | 2.37 | 1.90 |
| 70% | 2.62 | 2.10 |
| 65% | 2.91 | 2.33 |
| 60% | 3.25 | 2.60 |
| 55% | 3.69 | 2.95 |
| 50% | 4.29 | 3.43 |

Based on the above, the 1.0 support surface is expected to provide Dabir effects when operated at adjusted pressures of more than about 1.90 psi. When operated in such a manner, the 1.0 support surface overlay exhibits a nodal contact area density of less than about 75% area contact and, therefore, satisfies Criterion C above.

Based on the foregoing testing, the 1.0 support surface exhibits the % linear non-contact area vs. inflation pressure characteristics shown in Table 3.

TABLE 3

| Pressure (psi) | % Linear Non-Contact |
| --- | --- |
| 1.5 | 0.0 |
| 3.0 | 42.2 |
| 6.0 | 50.8 |
| 9.0 | 53.7 |
| 12.0 | 58.3 |
| 15.0 | 60.0 |

Figure 12B:
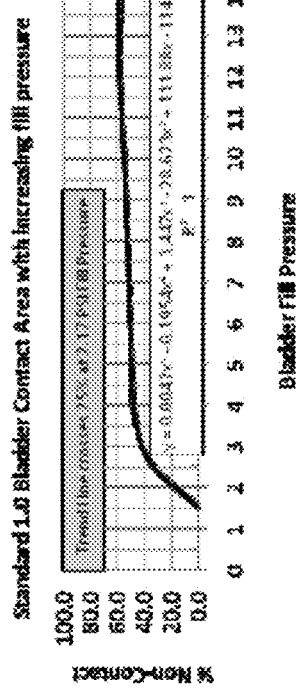
FIG. 12B is a plot of linear non-contact vs. inflation pressure for an exemplary support surface overlay.

The contact patterns that resulted from the foregoing testing are illustrated in FIG. 11. FIG. 12B is a plot of linear non-contact vs. inflation pressure using the data from Table 3. This data was used to derive Equation 4 defining % linear non-contact (y) as a function of fill pressure (x):

$$y = 0.0042x^5 - 0.1954x^4 + 3.447x^3 - 28.623x^2 + 111.88x - 114.09 \quad \text{(Equation 4)}$$

at $R^2 = 1$. Solving for fill pressure (x) at linear non-contact values of 25%-50% in 5% increments yields fill pressures as a function of linear non-contact as set forth in Table 4. Table 4 also sets forth an adjusted pressure as a function of % linear non-contact, the adjusted pressure being 20% lower than the pressure obtained from Equation 4. The adjusted pressure is intended to adjust for measurement and other errors that may occur during testing.

TABLE 4

| % Linear Non-Contact | Pressure (psi) | Adjusted Pressure (psi) |
| --- | --- | --- |
| 25% | 2.17 | 1.74 |
| 30% | 2.36 | 1.89 |
| 35% | 2.58 | 2.06 |
| 40% | 2.85 | 2.28 |
| 45% | 3.23 | 2.58 |
| 50% | 3.91 | 3.13 |

Based on the above, the 1.0 support surface overlay is expected to provide Dabir effects when operated at adjusted pressures of at least 1.74 psi. When operated in such a manner, the 1.0 support surface overlay exhibits a nodal linear non-contact pattern of 25% or more non-contact and, therefore, satisfies Criterion D above.

The 1.3 support surface overlay is substantially identical to the 1.0 support surface overlay but is dimensionally larger by a nominal factor of 1.3. The 1.3 support surface overlay is characterized by inflatable cells 120 having a nominal diameter of 1.06 inches, nominal horizontal spacing of 1.69 inches and nominal vertical spacing of 1.59 inches, a thickness of 0.661 inches a nodal contact density of 15 nodes per square decimeter. As such, the 1.3 support surface overlay satisfies Criteria A and B above. The 1.3 bladder is expected to satisfy Criteria C and D, as well.

Other examples could be made having other dimensions and satisfying one or more of Criteria A-D. Similar testing and methodology could be used to determine whether a bladder 100 having any dimensions would provide Dabir effects.

4. Control Systems

Figure 13:
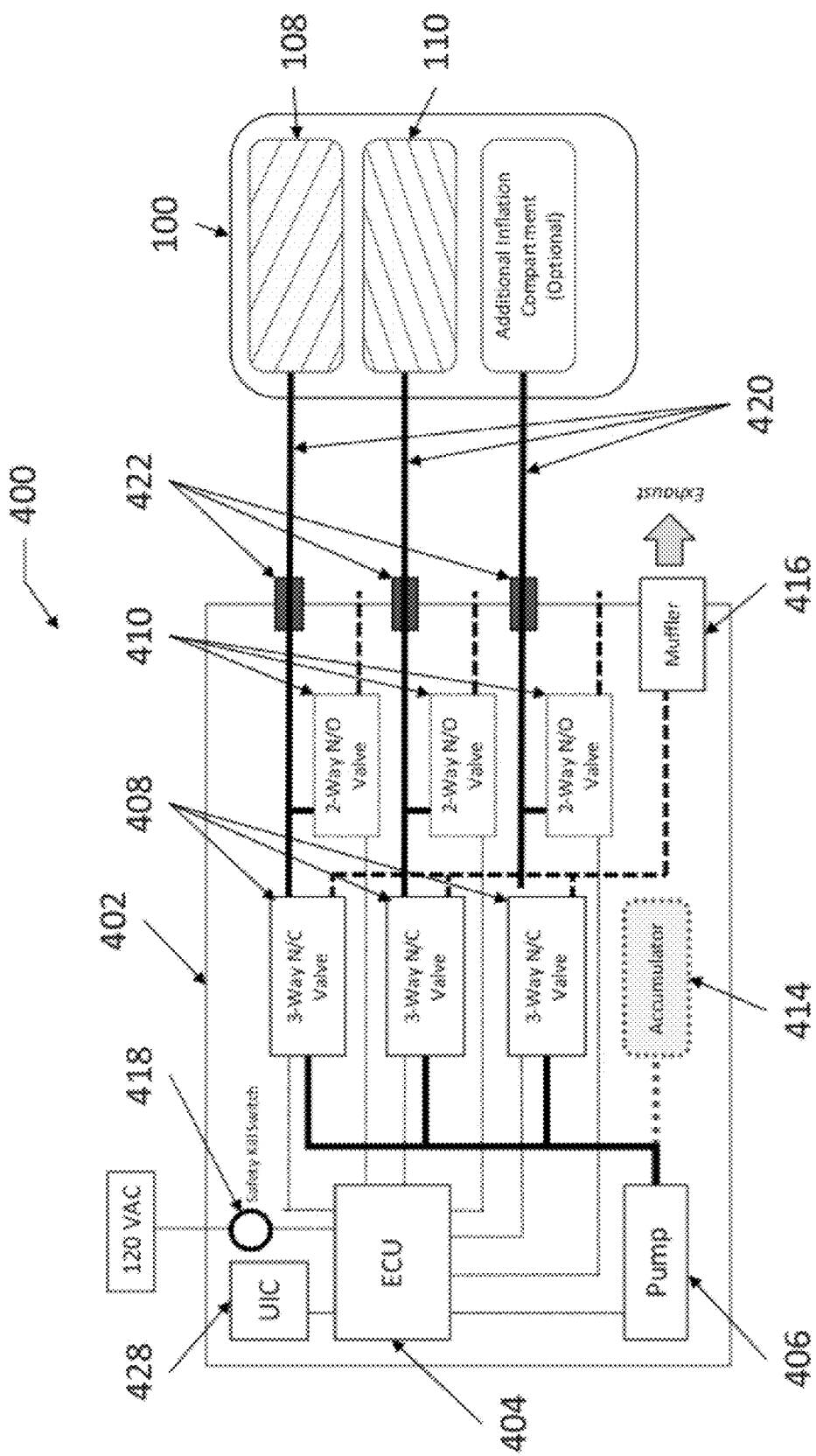
FIG. 13 is a schematic representation of an exemplary system for operating an exemplary support surface overlay.

As shown in FIG. 13, support surface overlay 100 can be included in a system 400 further including a pneumatic control system (PCS) 402 configured to control the inflation and deflation of first and second inflatable compartments 108, 110. (PCS 402 is illustrated as including optional means for controlling a third inflatable compartment.) PCS 402 may include a pneumatic pump 406, a plurality of regulator valves 408, and a plurality of dump valves 410 in fluid communication with fluid conduits 124, 126 of first and second inflatable compartments 108, 110 via pneumatic lines 420. Pneumatic lines 420 may be connected to PCS 402 and/or inflatable compartments 108, 110 of support surface overlay 100 via quick disconnect fittings 422 or by other suitable means.

Pump 406 may be embodied as any form of pump suitable for inflating inflatable compartments 108, 110 as discussed herein. For example, pump 406 could be embodied as a scroll pump having PWM drive control allowing for duty cycle control sufficient to enable direct inflation of inflatable compartments 108, 110 without the need for an accumulator. In some embodiments, PCS 402 could be supplied with air from an external source, for example, a hospital's high pressure air system. In such embodiments, pump 406 could be bypassed or omitted.

Regulator valves 408 provide a means to charge inflatable compartments 108, 110 with fluid. Dump valves 410 provide a means for allowing all of inflatable compartments 108, 110 to be rapidly deflated upon demand, for example, in the event of a need to perform CPR on a patient lying on the device (CPR might not be effectively performed upon a patient lying on the device with one or more of inflatable compartments 108, 110 inflated). Dump valves 410 could be omitted if desired, particularly in embodiments in which regulator valves 408 provide sufficient reverse flow capacity. A separate and independently controlled regulator valve 408 and dump valve 410 may be provided for each of first inflatable compartment 108 and second inflatable compartment 110. In some embodiments, however, a single regulator valve 408 and dump valve 410 could control inflation and deflation of both first inflatable compartment 108 and second inflatable compartment 110.

PCS 402 may also include an accumulator 414, an exhaust muffler 416, and/or a safety kill switch 418. Accumulator 414 could be provided to store pressurized air for operation of bladder 100, and exhaust muffler 416 could be provided to silence air as it escapes bladder 100. An intake muffler and replaceable intake filter are not shown but also could be provided to silence and filter air being drawn into pump 406. Safety kill switch 418 could be provided to shut off power to PCS 402, as may be desired by an operator.

In some embodiments (not shown), PCS 402 could be configured to provide pneumatic control for more than one bladder 100. For example, a single regulator valve 408 and single dump valve 410 could be in fluid communication with the first inflatable compartment 108 and/or second inflatable compartment 110 of two or more support surface overlays 100. Alternatively, PCS 402 could include a first pneumatic pump 406 and first set of regulator and dump valves 408, 410 for a first support surface overlay 100 and an additional pneumatic pump 406 and additional sets of regulator and dump valves 408, 410 for each additional support surface overlay 100.

PCS 402 or any portion thereof may be provided in a portable case so that these components may be easily transported as a unit.

PCS 402 may include an electronic control unit (ECU) 404 that controls pump 406 and valves 408, 410, thereby controlling the inflation and deflation of inflatable compartments 108, 110. ECU 404 may be pre-programmed to selectively inflate and deflate first and/or second inflatable compartments 108, 110 according to any number and variety of patterns and/or cycles. Also, ECU 404 may include a user interface console (UIC) 428 having a user interface panel 430 through which a user can select any particular inflation/deflation pattern or cycle into ECU 404 and/or otherwise control the operation of ECU 404. In other embodiments, ECU 404 could enable a user to create custom inflation/deflation patterns or cycles or manually control PCS 402. UIC 428 could be tethered to ECU 404 or it could control ECU 404 wirelessly.

Figure 14:
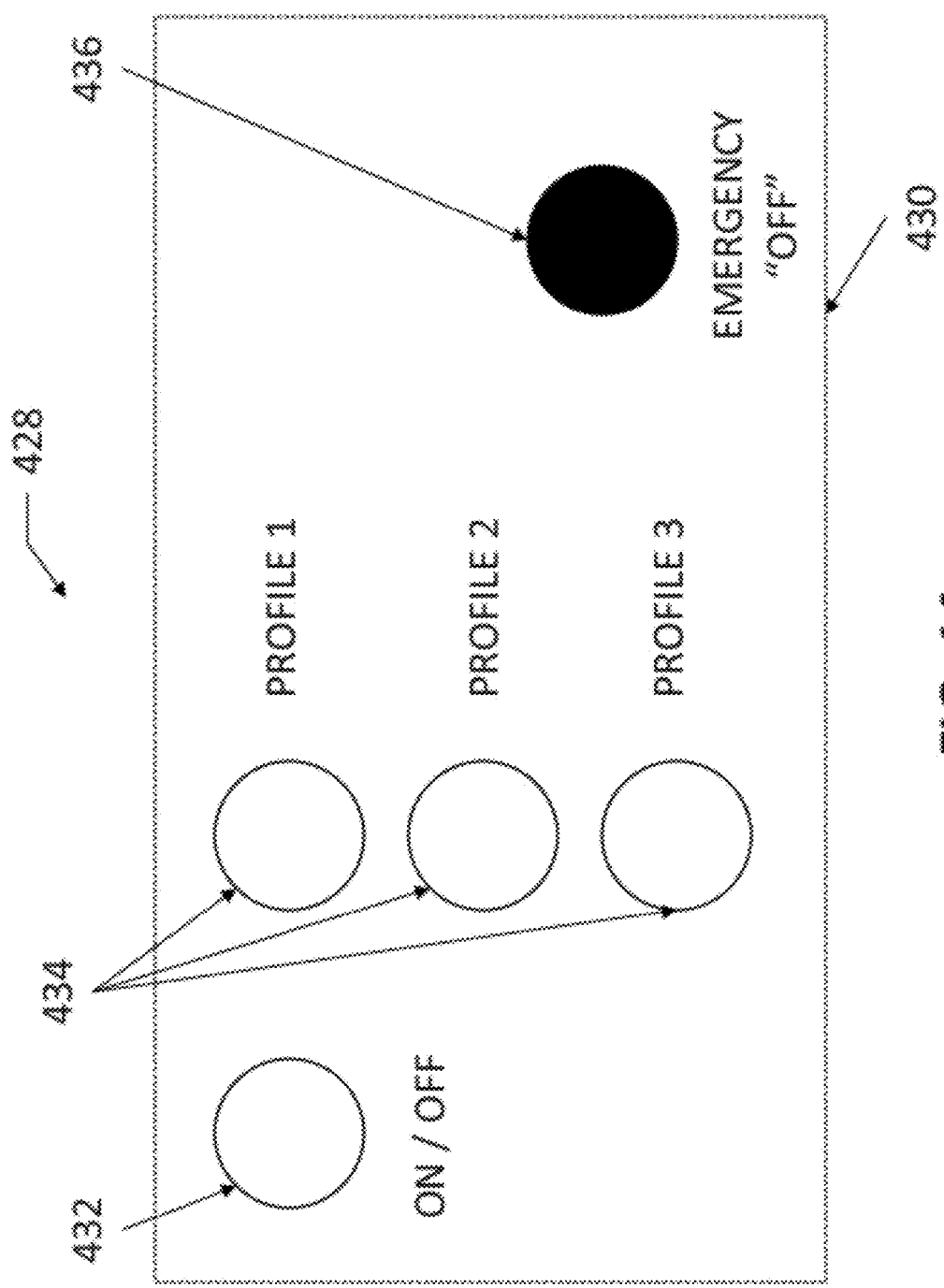
FIG. 14 is a layout drawing of an exemplary control panel for use with the system shown in FIG. 13.

With reference to FIG. 14, user interface panel 430 may include an on/off switch 432, a plurality of profile switches 434, and an emergency off switch 436. On/off switch 432 allows a user to toggle PCS 402 on and off. Each of profile switches 434 is associated with a particular, predefined pattern and cycle of inflation, dwell, and deflation of first and second inflatable compartments 108, 110. The pattern and cycle of inflation/dwell/deflation associated with each profile switch 434 can, for example, be started by selecting that profile switch 434 a first time and stopped by selecting that profile switch 434 a second time. The emergency stop switch 436 can be used to, for example, turn off pump 406 and rapidly deflate support surface overlay 100 in the case of an emergency, for example, in the event CPR needs to be used on a person lying on support surface overlay 100. Each of the foregoing switches can include visual, audible, and vibratory haptic feedback mechanisms to assist the user in confirming which switches and/or modes of operation of PCS 402 have been selected.

Figure 15:
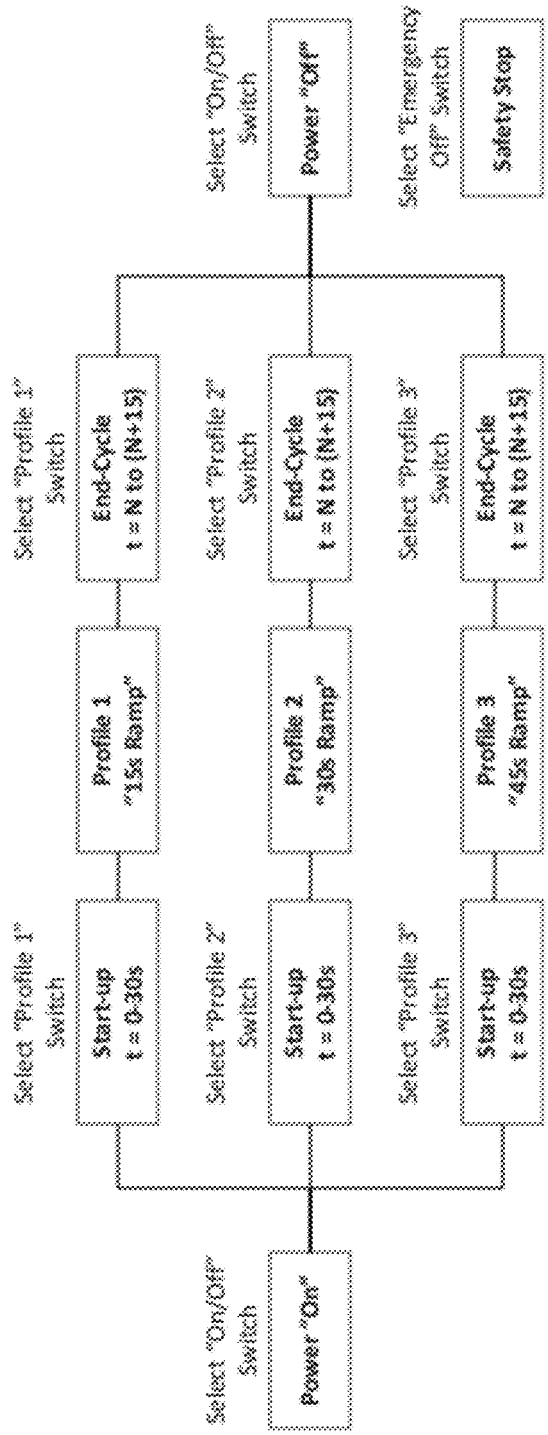
FIG. 15 is a block representation of various operating modes of an exemplary system for operating an exemplary support surface overlay.

A block diagram illustrating an example of the functions (for example, exemplary inflation/deflation times and patterns for "Profile 1", "Profile 2", and "Profile 3") associated with each of those switches is provided in FIG. 15.

Figure 18:
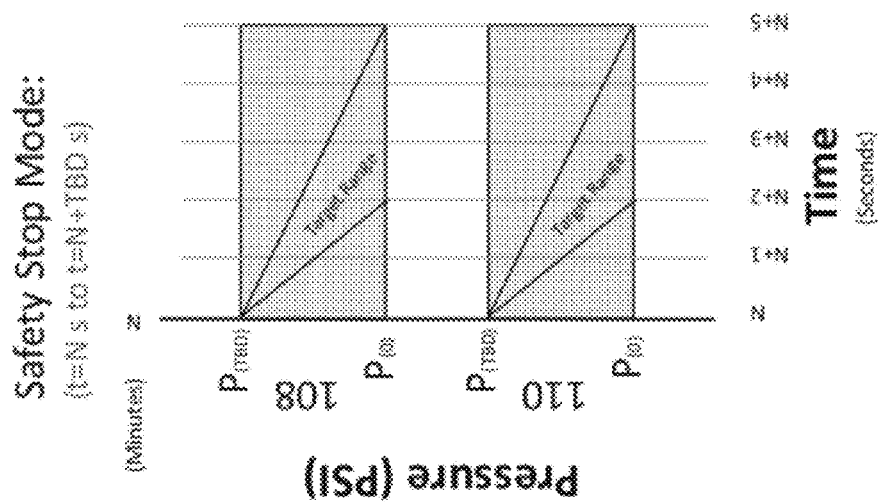
FIG. 18 is a graphic representation of an exemplary safety stop cycle mode for an exemplary system for operating an exemplary support surface overlay.
Figure 17:
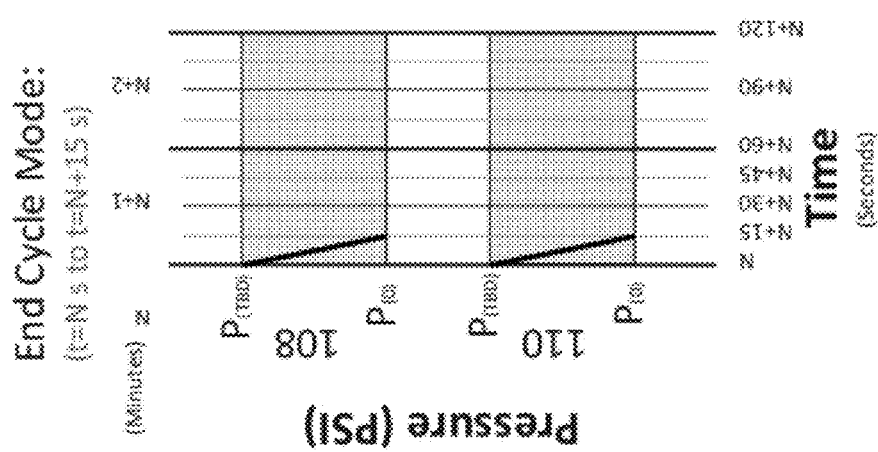
FIG. 17 is a graphic representation of an exemplary end cycle mode for an exemplary system for operating an exemplary support surface overlay.
Figure 16:
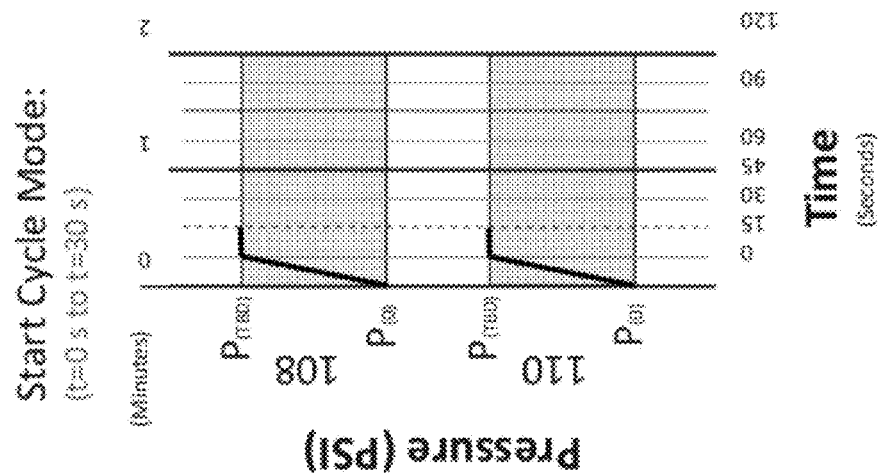
FIG. 16 is a graphic representation of an exemplary start cycle mode for an exemplary system for operating an exemplary support surface overlay.

FIGS. 16-21 illustrate examples of various predefined patterns and cycles of inflation, dwell and deflation of first and second compartments 108, 110. As FIG. 16 illustrates, inflatable compartments 108, 110 could be inflated when one of switches 434 is selected. This initial inflation may take a predetermined amount of time, for example, about 15 seconds. After an optional, predetermined dwell time, for example, 15 seconds, one of the patterns and cycles can begin. As FIG. 17 illustrates, both of inflatable compartments 108, 110 can be deflated after a pattern and cycle of inflation/deflation is complete, which also can take about 15 seconds—unless the pattern and cycle is stopped when inflatable compartments 108, 110 are not fully inflated, in which case it will take less than 15 seconds. As FIG. 18 illustrates, both of inflatable compartments 108, 110 can be deflated in 5 seconds or less if the emergency off switch 436 is actuated.

Figure 19:
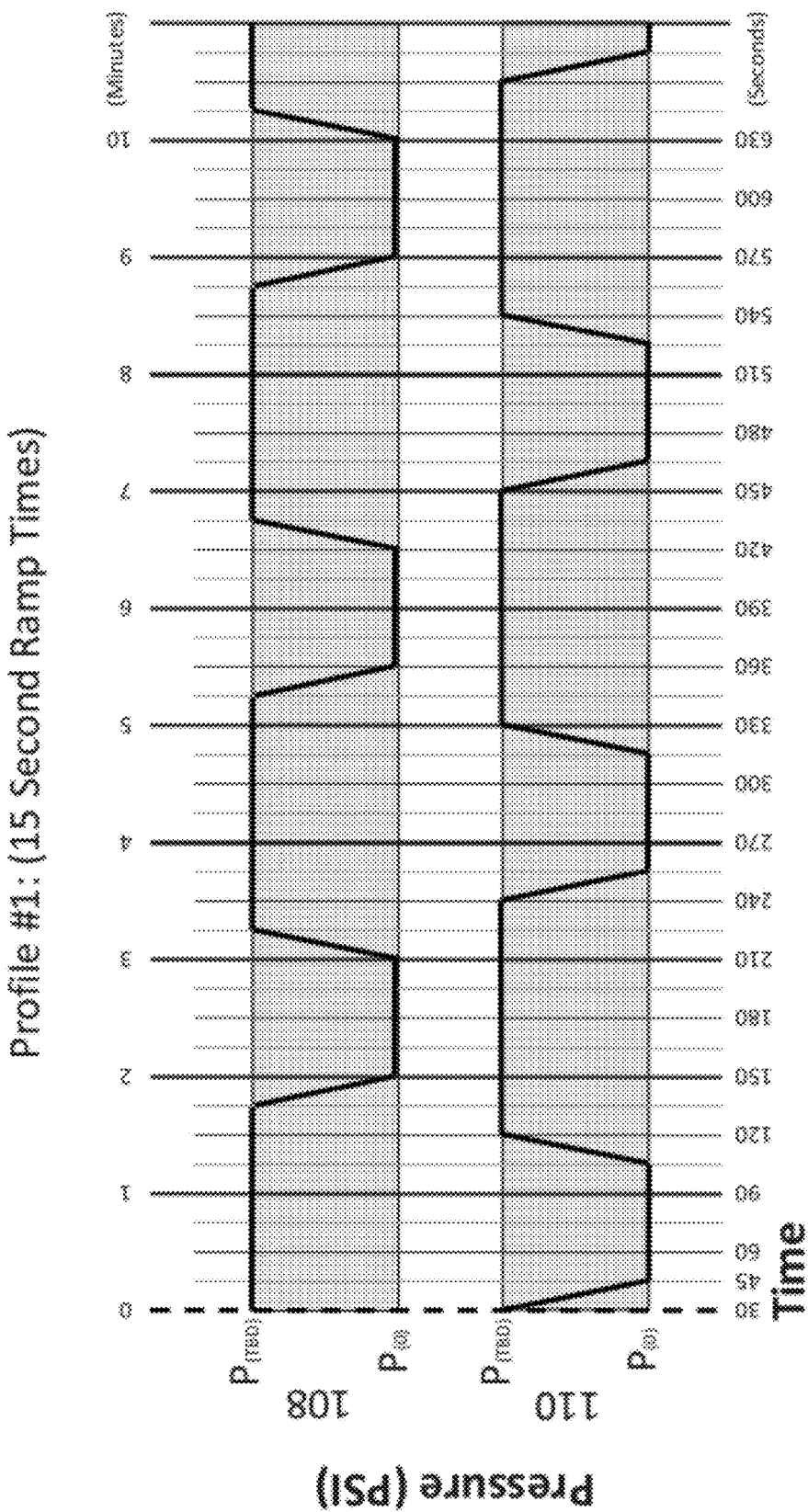
FIGS. 19-21 are graphic representations of several predefined patterns and cycles of inflation/deflation of an exemplary system for operating an exemplary support surface overlay.
Figure 20:
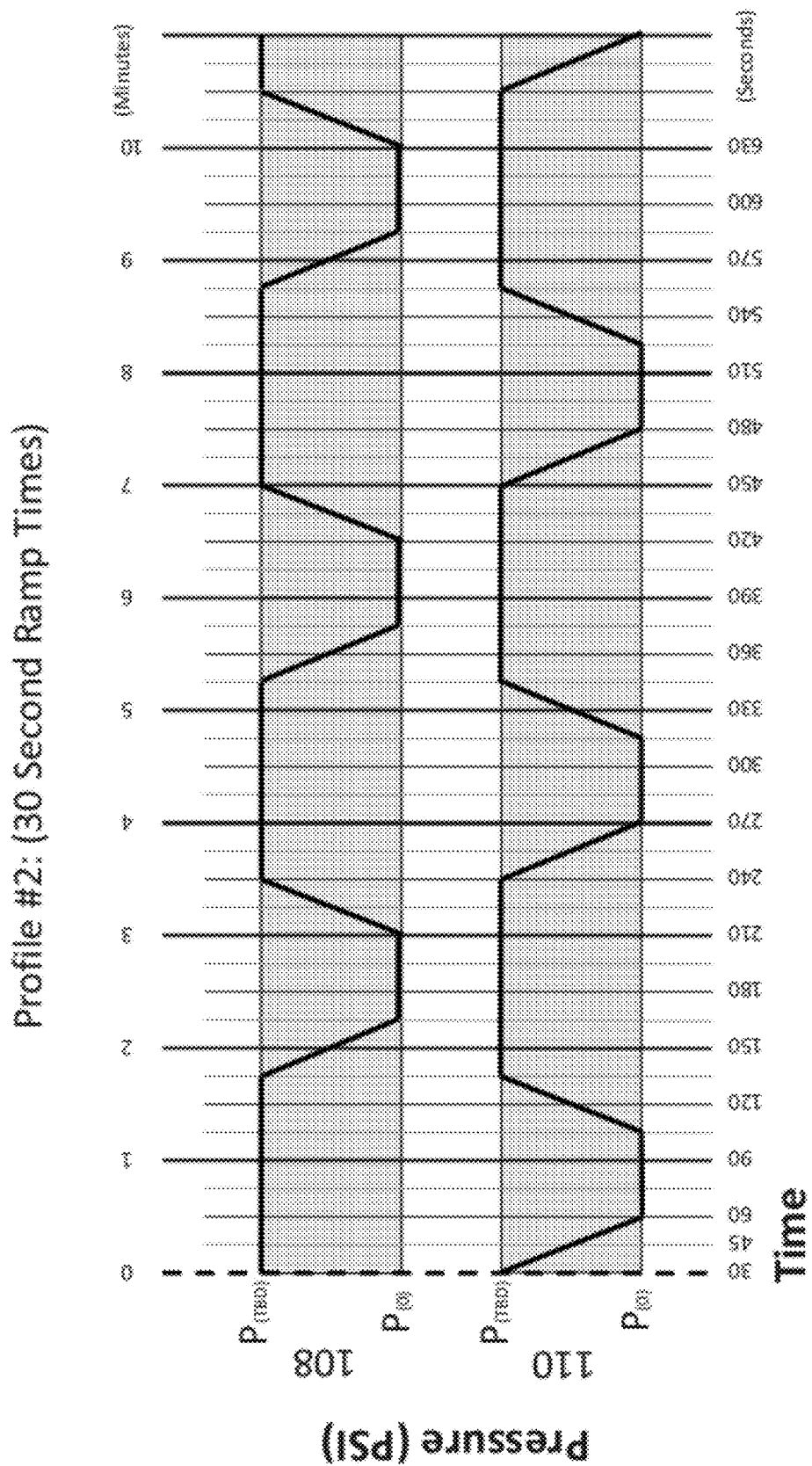
Figure 21:
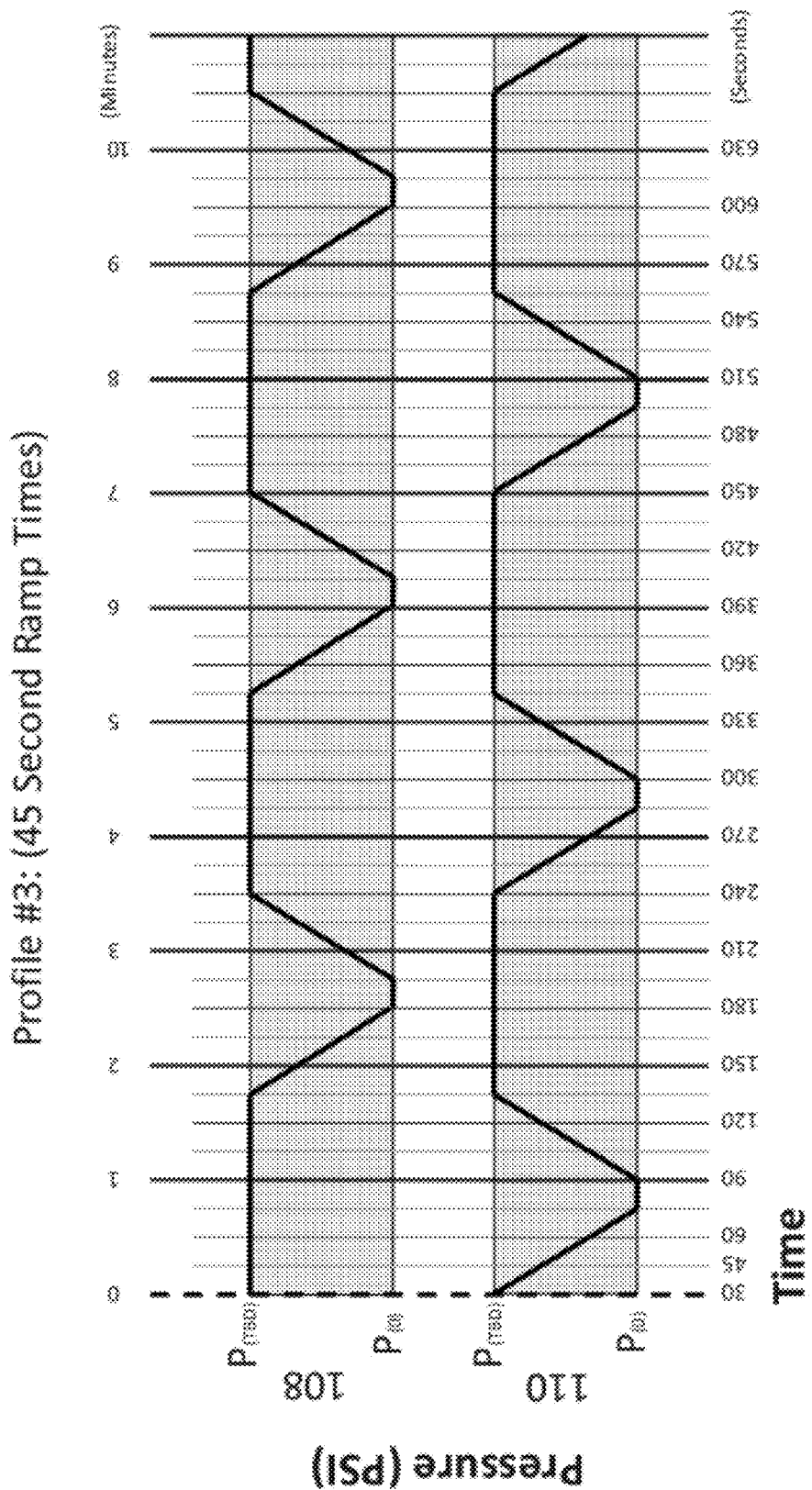

FIG. 19 illustrates the pattern and cycle associated with first profile switch 434 ("Profile 1"); FIG. 20 illustrates the pattern and cycle associated with second profile switch 434 ("Profile 2"); and FIG. 21 illustrates the pattern and cycle associated with third profile switch 434 ("Profile 3"). Although each of those figures illustrates linear inflation and deflation rates, such linearity is not required.

Although the user interface is described above as only having three different, predefined patterns and cycles of inflation/deflation, it can provide functionality by which a user can define and store other patterns and cycles of inflation/deflation and assume full manual control over the inflation and deflation of first and second inflatable compartments 108, 110. UIC 428 provides the main point of input from the doctor, nurse, or patient and controls the patterns and cycles of inflation/deflation by controlling solenoids that open and close regulator valves 408 and dump valves 410. It also can control pressure regulators that determine and control inflation pressures in first and second inflatable compartments 108, 110 and operation of pneumatic pump 406. ECU 404 can also be programmed to monitor, control, and collect data from sensors that examine load, pressure, temperature, and moisture, with or without respect to time.

The operation of ECU 404 and PCS 402 preferably are implemented using a suitable computing processor or processing platform that is capable of performing the functions and operations in accordance with the invention. Each of those devices may include a user interface and/or display for operating the computing processor or processing platform. All or parts of the system and processes can be stored on or read from a memory or computer readable media.

PCS 402, ECU 404, and pneumatic pump 406, and valves 408, 410 may be battery powered (VDC) or wall outlet powered (VAC). System 400 preferably operates at a noise level lower than 40 dB and can cycle a 400 pound load at least 10,000-25,000 times. Preferably, the maximum continuous current draw of each component is 5 amps.

In certain embodiments, PCS 402 could be replaced or supplemented with an analogous system configured to inflate and deflate inflatable compartments 108, 110 using another gas or a liquid instead of air, as would be understood by one skilled in the art.

The control system could be set up to synchronize the inflation and/or deflation of inflatable compartments 108, 110 to natural body or environmental rhythms, for example, heartbeat, pulse, respiration rate. Doing so could have a beneficial psychological or therapeutic effect. The control system also could include means for effecting active noise cancellation to further muffle sounds made by system 400.

Support surface overlay 100 may be provided with means, for example, a one-time programmable (OTP) chip including the support surface's serial number, for self-identification when connected to a control system, as well as means, for example, an erasable programmable memory (EPROM) for storing other information relevant to the bladder, for example, the number of inflation/deflation cycles it has been subjected to. The control system could be configured to not operate a bladder if the control system does not recognize the bladder's serial number or if it determines that the bladder has been used for an excessive number of cycles.

The control system also could be adapted to interface with a computer network to allow remote indication of the operation and status of the system, including any faults or alarms. For example, the control system could output alarms indicative of the need for filter replacement or other maintenance, the number of inflation/deflation cycles support surface overlay 100 has been subjected to, attempts to connect to the control system a support surface overlay 100 having a serial number not recognized by the system, and the like.

5. Anti-Shear Provisions

Support surface overlay 100 may have a propensity to contract from side to side and/or end to end when either or both of first inflatable compartment 108 and second inflatable compartment 110 are inflated, as would be recognized by one skilled in the art. Such contraction may cause shearing or tearing of tissue of a user disposed on support surface overlay 100, as would be understood by one skilled in the art.

Figure 6:
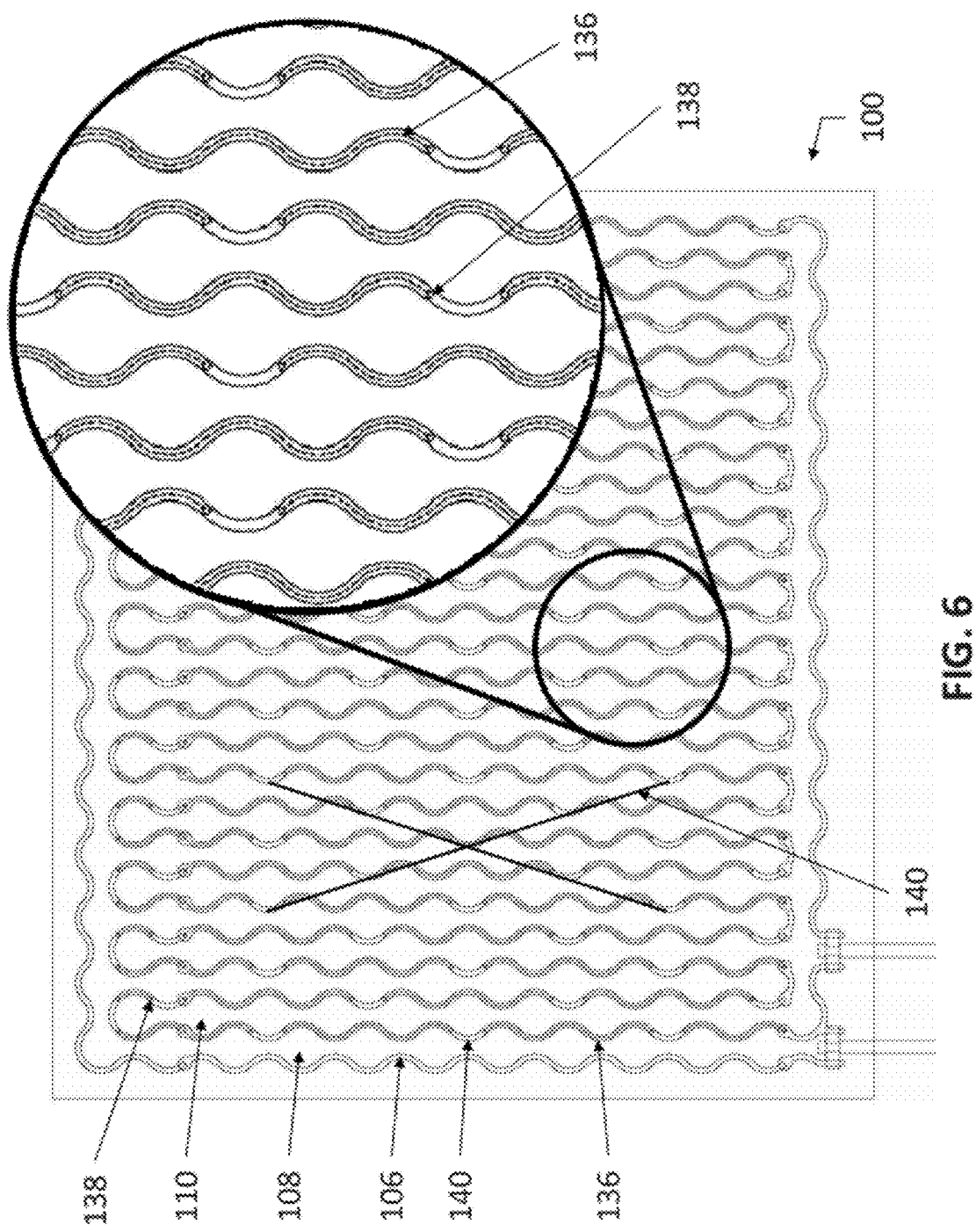
FIG. 6 is a plan view of a support surface overlay having relief cuts formed therein.

The foregoing contraction/shearing effect may be mitigated by providing support surface overlay 100 with optional relief cuts 136 perforating upper sheet 102 and lower sheet 104 of support surface overlay 100 between adjacent inflatable rows 114, 118 of first and second inflatable compartments 108, 110, for example, as shown in FIG. 6. Relief cuts 136 can be formed in support surface overlay 100, for example, within the confines of seams 106 or elsewhere without penetrating the pressure boundaries of first inflatable compartment 108 or second inflatable compartment 110. Relief cuts 136 can be formed by any suitable means, for example, by die, knife or laser cutting. A circular stress relief 138 can be provided at each end of each relief cut.

Relief cuts 136 allow displacement of certain portions of support surface overlay 100 in response to inflation of first inflatable compartment 108 and/or second inflatable compartment 110 while mitigating side-to-side and/or end to end contraction of support surface overlay 100 and corresponding displacement of inflatable cells 120 and contact nodes 122 while under load. In the FIG. 6 embodiment, relief cuts 136 are elongated and provided in a so-called 3-1 pattern, wherein a relief cut 136 is provided over $5\pi$ radians of every $6\pi$ radians of sinusoidally-shaped seams 106 defining an inflatable row 114, 118 of an inflatable compartment 108, 110. In this embodiment, every third "trough" of each seam 106 defining an inflatable row 114, 118 of an inflatable compartment 108, 110 lacks a relief cut 136. These uncut regions 140 form an X-pattern, as shown in FIG. 6.

In other embodiments, support surface overlay 100 could be provided with more or fewer relief cuts 136 than shown in FIG. 6 and/or in different patterns than shown in FIG. 6. For example, relief cuts 136 could extend over as few as $\pi$ radians of every $2\pi$ radians or less, or over the full extent of rows 114, 118 from manifold 112 to manifold 116. In support surface overlays 100 not having sinuous seams 106, relief cuts 136 could be provided between rows of inflatable compartments in a similar manner, as would be understood by one skilled in the art.

Relief cuts 136 can be, but need not be, provided throughout substantially the entirety of support surface overlay 100 or a lesser portion of support surface overlay 100. The pattern of relief cuts 136 shown in FIG. 6, when provided throughout substantially the entirety of support surface overlay 100, may substantially mitigate side-to-side and/or end-to-end contraction of support surface overlay 100 upon inflation of first inflatable compartment 108 and/or second inflatable compartment 110 while supporting a user.

Figure 24:
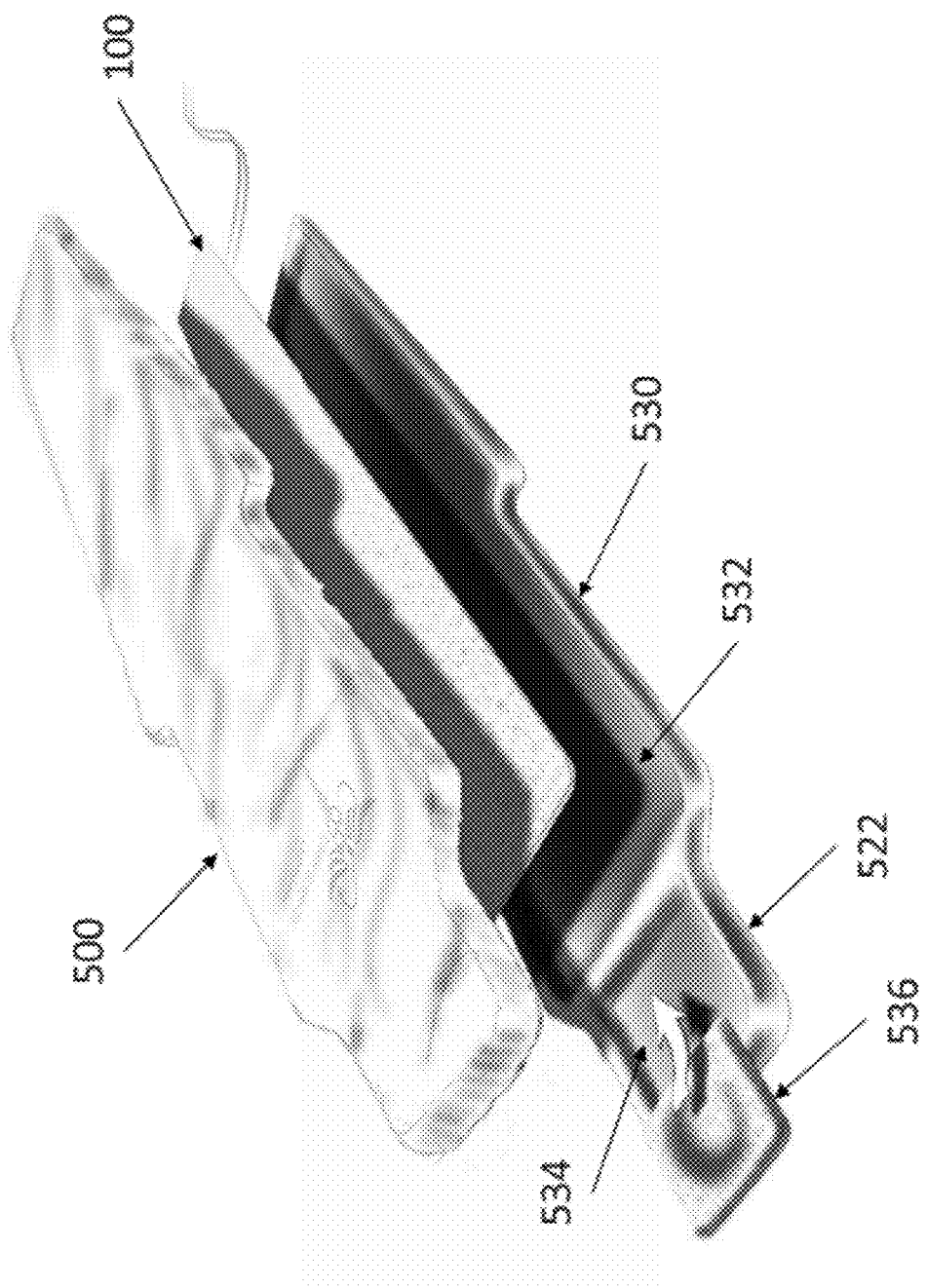
FIG. 24 is a perspective view of an exemplary liner bag and foam insert in combination with an exemplary support surface overlay.

The foregoing contraction/shearing effect also may be mitigated by means of an anti-shear liner (for example, liner bag 500 as shown in FIG. 24) loosely fit over or around support surface overlay 100. Such a liner may be made of a single layer of material sufficiently slippery to not securely adhere to either or both of support surface overlay 100 and a user disposed thereon under shearing loads that might be produced when inflatable compartments 108, 110 of support surface overlay 100 are inflated and deflated. Alternatively, such a liner may be made of two layers of material, for example, rip-stop nylon, sufficiently slippery to not securely adhere to each other under shearing loads that might be produced when inflatable compartments 108, 110 of support surface overlay 100 are inflated and deflated. Anti-shear liners, when provided, preferably would be readily removable from support surface overlay 100 and machine washable or otherwise readily cleanable.

Figure 27B:
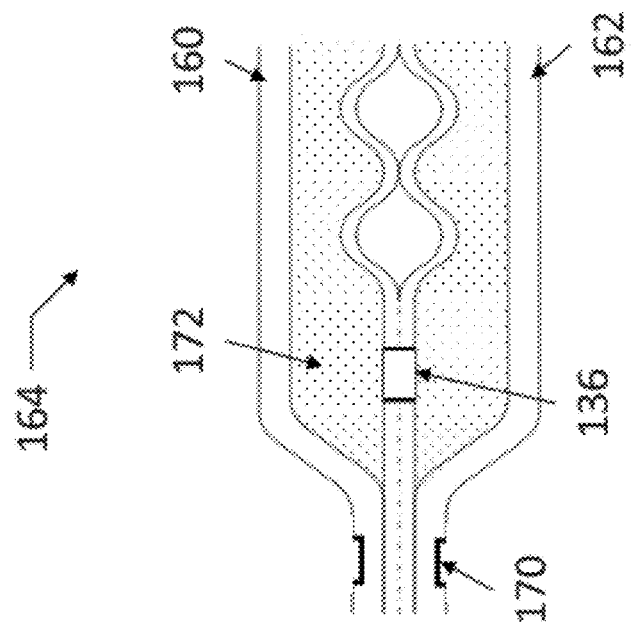
FIG. 27B is a section view of the support surface overlay of FIG. 27A.
Figure 27A:
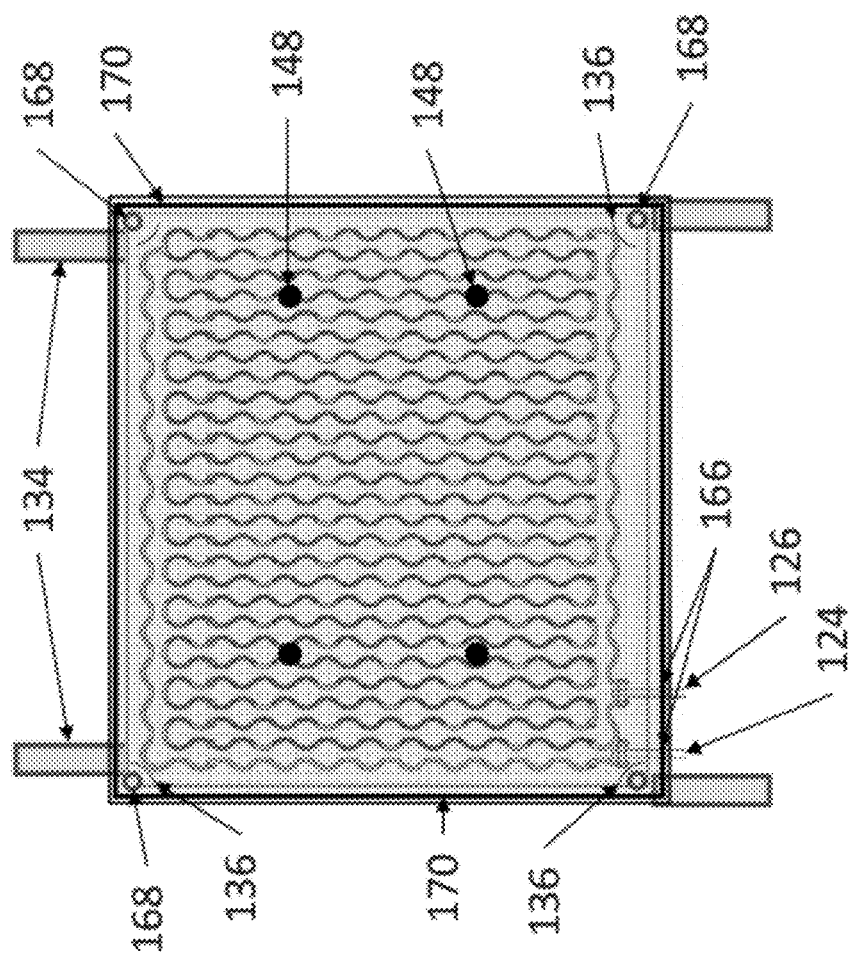
FIG. 27A is a top plan view of a support surface overlay disposed within a housing also containing a lubricating fluid.

In another embodiment, shown in FIGS. 27A and 27B, support surface overlay 100 could be contained within substantially fluid-tight envelope 164 made, for example, of an upper sheet 160 and a lower sheet 162 joined together in a substantially fluid-tight manner, for example, by a perimeter seal 170 (which could be an RF weldment). Envelope 164 could include sealing grommets 166 for receiving fluid conduits 124, 126 in a generally fluid-tight manner.

Envelope 164 could be attached to corners of support surface overlay 100 by RF spot welds 168 or otherwise. Alternatively, support surface overlay 100 could "float" within envelope 164. Additional spot welds 148 could be provided to prevent undue ballooning of envelope 164 when pressurized. Relief cuts 136 could be provided in support surface overlay 100 proximate the corners thereof. The interior region of envelope 164 could be filled with a lubricating fluid 172 or other substance enabling support surface overlay 100 to expand and contact within envelope 164 without imparting substantial shear forces on a user disposed thereon.

In another embodiment, a support surface overlay 100 including or not including relief cuts 136 could be encapsulated in a self-skinned foam liner. In such an embodiment, the foam liner could absorb or otherwise mitigate shearing effects, provide comfort and be easily cleanable.

6. Microclimate Control

Support surface overlay 100 can further be configured to allow for control of the microclimate about a user disposed on support surface overlay 100 by incorporating a ventilation and air conditioning system that discharges air or another medium into the region about the upper side of support surface overlay 100. For example, upper sheet 102 of support surface overlay 100 could be made of a material sufficiently permeable to enable controlled release of air therefrom to provide climate control, yet sufficiently fluid-tight to allow for inflation of inflatable compartments 108, 110 as discussed above. In such an embodiment, a suitable sealant (not shown) could be applied to selected portions of upper sheet 102. The sealant would preclude fluid from flowing through portions of upper sheet 102 to which the sealant had been applied. This technique can be used to effect better distribution of fluid flow through upper sheet 102. Alternatively, upper sheet 102 could be perforated with small holes (not shown) at predetermined locations in order to provide a controlled release of air. The released air can be channeled through the interstitial regions defined by inflatable cells 120, contact nodes 122 and a user lying thereon.

In another embodiment, as shown in FIGS. 25A-25D, a third sheet 142 could be attached to the lower side of support surface overlay 100 such that third sheet 142 and support surface overlay 100 form a plenum 144 there between. For example, third sheet 142 could be RF welded to a peripheral portion of lower sheet 104 or another portion of support surface overlay 100 by means of perimeter weld 146 to form plenum 144. Third sheet 142 also could be attached to portions of support surface overlay 100 within the peripheral portion thereof by means of one or more spot welds 148 or otherwise in order to prevent ballooning of plenum 144 when the plenum is pressurized, as discussed below. Preferably, third sheet 142 is substantially impermeable and sufficiently flexible to not adversely affect inflation and deflation of inflatable compartments 108, 110. Third sheet 142 could be made of the same material used to make first and second sheets 102, 104.

An air inlet tube 150 could be provided in fluid communication with this plenum to allow introduction of air or another medium to the plenum. Support surface overlay 100 could include perforations, for example, at predetermined locations in seams 106 through which this air could escape and provide ventilation to a user lying on a support surface overlay 100. Such perforations could be embodied as relief cuts 136. In embodiments not including relief cuts 136, such perforations could take other forms, for example, ventilation ports 152. Some embodiments could include relief cuts 136 and ventilation parts 152. As set forth above, the released air can be channeled through the interstitial regions defined by inflatable cells 120, contact nodes 122 and a user lying thereon.

An optional fourth sheet 154 as shown in FIGS. 25B-25C (optional fourth sheet 154 is not shown in FIGS. 25A and 25D for clarity) may be attached to the upper side of support surface overlay 100. Fourth sheet 154 preferably would be made of a material, for example, nonwoven TPU fabric, sufficiently permeable to allow ventilating air escaping from the plenum to pass there through and into the interface region between support surface overlay 100 and a user disposed thereon. Fourth sheet 154 could be made of a material that also provides anti-shear characteristics, as discussed above.

Supply air for plenum 144 could be provided from various sources. For example, the exhaust from inflatable compartments 108, 110 could be discharged into plenum 144 and thereby be used as ventilating air. PCS 402 could be modified to include additional valving and control logic to enable such a flow path. Alternatively, supply air for plenum 144 could be provided separately, either from pump 406 or another source (not shown).

The air supplied to plenum 144 could be heated cooled, humidified, dehumidified, or otherwise conditioned to enhance the health and/or comfort of a user disposed on support surface overlay 100. Also, drugs, antiseptics or other media could be added to the air supplied to plenum 144 for delivery to the region about the upper side of support surface overlay 100.

A heating element could be provided behind support surface overlay 100 to provide additional heating. A carbon fiber heating element could be used to maintain x-ray translucency.

7. Peripheral Support Elements and Enclosures

Figure 22:
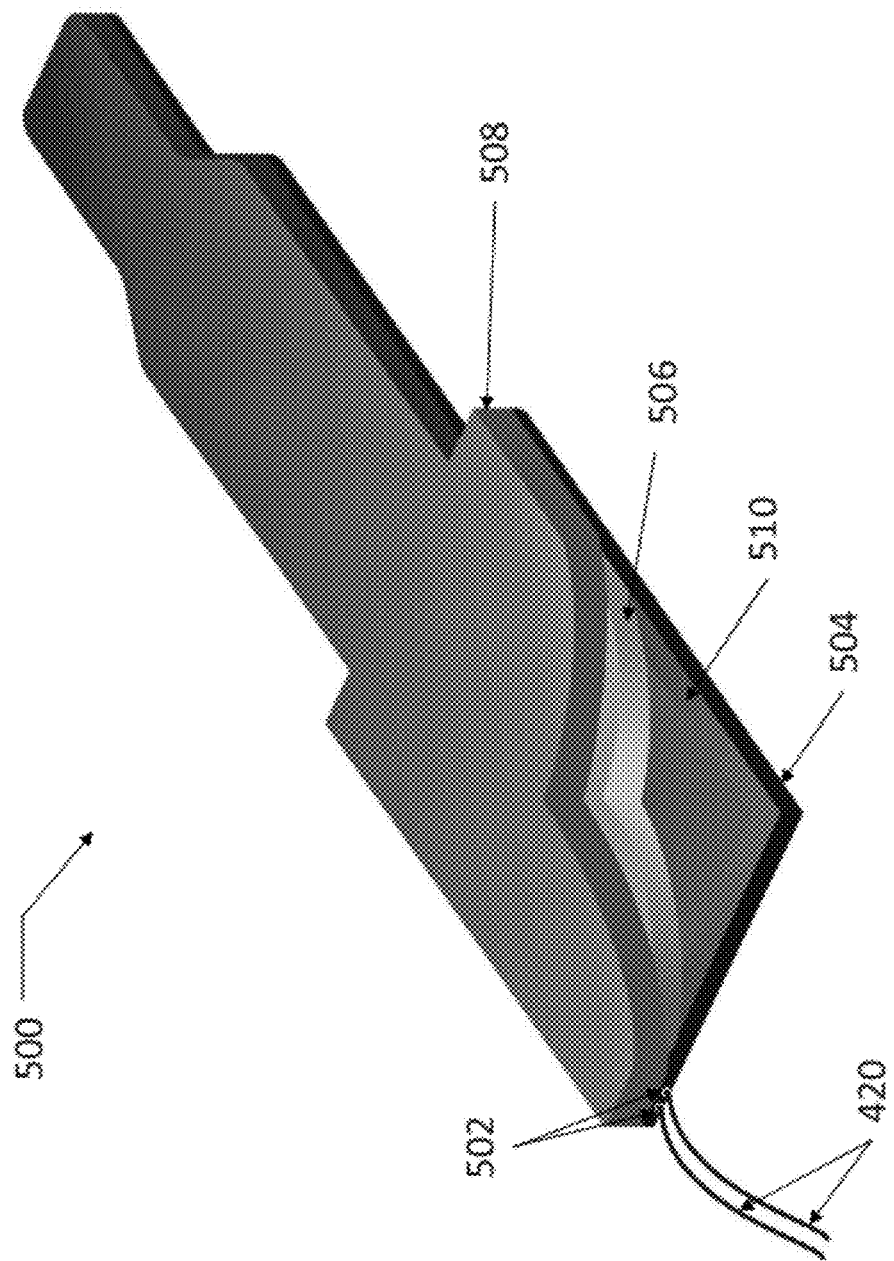
FIG. 22 is a perspective view of an exemplary liner bag for use in connection with an exemplary support surface overlay.

System 400 may also include a double thickness liner bag 500 (see FIG. 22), a foam mat (not shown), a head rest 522 (see FIG. 23), inflatable side bladders 524 (see FIG. 32), and a dynamic edge rail 526 (see FIG. 32). Liner bag 500 can substantially envelop support surface overlay 100, the foam mat, head rest 522, inflatable side bladders 524, and dynamic edge rail 526, thereby forming pad 520. Liner bag 500 may enclose the foregoing components using a medical grade ziploc or zipper system (not shown) that allows for easy disassembly of top and bottom portions for quick maintenance and/or replacement.

Liner bag 500 can assist in providing patient comfort and protecting pad 520, while allowing substantially uninhibited operation of inflatable compartments 108, 110 of support surface overlay 100. Liner bag 500 may be designed to allow for slip between layers that provide low friction across its surfaces as well as elasticity so as to not impair the performance of support surface overlay 100. Also, liner bag 500 may stretch in a manner that allows for a user's weight to be supported by contact nodes 122 without bag 500 being ripped or torn or causing a hammock effect. Liner bag 500 may also be impervious to various fluids so as to protect pad 520 from foreign matter, such as urine, feces, blood, and alcohol. Liner bag 500 preferably can be easily removed and cleaned and/or be cleaned without being removed using inflatable side bladders 524 to pull the surface of liner bag 500 taut. In some embodiments, liner bag 500 could be made of or treated with an anti-bacterial/anti-microbial material. (Similarly, support surface overlay 100 could itself be treated with an anti-bacterial/anti-microbial material.)

Liner bag 500 may include one or more of: sealing grommets 502 that allow pneumatic lines 420 to be connected between inflatable compartments 108, 110 and pneumatic pump 406; a bottom layer 504 and straps (not shown) that hold liner bag 500 and its contents securely to a table, bed, or medical imaging device on which it may be used; an inner protective layer 506 for protecting pad 520 within liner bag 500 and protecting liner bag 500 from ripping or tearing; and a stretchable outer layer 508 that stretches as contact nodes 122 press against liner bag 500. Bottom layer 504 preferably is made of a fabric, for example, the SLIP-NOT brand fabric made by Eastex Products, Inc., that holds up strongly to wear and abrasion and also offers grip and non-skid performance under both wet and dry conditions. Inner protective layer 506 preferably is made of a nylon-reinforced rip-stop material. Stretchable outer layer 508 preferably is made of a fluid-proof and stain-resistant fabric, for example, the TEK STRETCH 2 brand fabric made by Eastex Products, Inc., that stretches in the two directions perpendicular to the plane of the fabric. The straps (not shown) preferably are made of nylon and preferably can support a 200 pound retention load. Liner bag 500 may also include an inner slip/shear reducer 510 disposed between non-slip bottom layer 504 and inner protective layer 506 to reduce slip/shear between those layers.

FIGS. 23A, 23B and 24 illustrate an example of a pad 520 that can be enclosed in liner bag 500. In the exemplary embodiment of pad 520 illustrated in FIG. 23A, a plurality of support surface overlays 100 are assembled in the shape of a catheter table, except for head rest 522, which is formed from a durable soft material. Pad 520 also includes inflatable side bladders 524 disposed along the sides of support surface overlay 100. Inflatable compartments 108, 110 are illustrated schematically in block form but in practice would take a form as discussed above in the detailed description of support surface overlay 100. Inflatable side bladders 524 can be positioned substantially perpendicular to the alternating rows of inflatable compartments 108, 110. Preferably, inflatable side bladders 524 are thicker when inflated than inflatable compartments 108, 110. For example, inflatable side bladders 524 can be approximately 1½ inches wide and 1½ inches thick. The catheter table, not including head rest 522, can be approximately 100 inches long, approximately 24 inches wide at its widest point, and approximately 14 inches wide at its narrowest point. In an exemplary embodiment as illustrated in FIG. 23, inflatable compartments 108, 110 each have a volume of approximately 875 in$^3$, and inflatable side bladders 524 have a volume of approximately 450 in$^3$. Dimensioned as such, inflatable side bladders 524 can be inflated and deflated in about the same amount of time as each of first and second inflatable compartments 108, 110 (e.g., 15 seconds) at about half the flow rate (for example, about 2.0 CFM versus about 1.0 CFM). Other configurations, other dimensions, and other flow rates may be implemented as desired to suit other applications and to fit different tables, beds, and medical imaging devices. The dimensions and volumes of inflatable compartments 108, 110 and inflatable side bladders 524 may also be different based on the application and the desired performance, such as the flow rate required to fill them.

Inflatable side bladders 524 can be inflated in a cleaning mode to facilitate cleaning of liner bag 500. The cleaning mode stretches liner bag 500 to remove any wrinkles or folds therefrom so that the entire external surface of the liner bag 500 can be more easily wiped or otherwise cleaned. Side bladders 524 also can incorporate a secondary chamber to provide a dynamic edge rail 526. Dynamic edge rail 526 comprises a further inflatable zone that can be inflated or deflated as desired, for example, to provide side bolstering for a patient. In the alternative, the dynamic edge rail 526 can be formed from a durable soft material that is attached or to otherwise positioned at the sides of support surface overlay 100.

As an alternative to forming support surface overlays 100 in the shape of the load-bearing device on which they will be used, support surface overlays 100 can be made in a standard, modular configuration and disposed on a foam insert 530 that is formed in the shape of the load-bearing redistribution device on which support surface overlay 100 is to be used. Thus, instead of providing support surface overlays 100 in several shapes and sizes to conform to the shape of different load bearing devices, foam insert 530 can be formed to the shape of different load-bearing devices providing the base support for support surface overlay 100. Modifying the shape of foam insert 530 for each different load-bearing device may be easier and less costly than modifying support surface overlays 100 for specific applications. Foam insert 530 preferably is made of a medium density medical grade cellular urethane foam, such as the PORON brand foam made by Stockwell Elastomerics, Inc. Different and/or additional materials may also be used to construct liner bag 500 depending on the application and the desired attributes of liner bag 500.

As illustrated in FIG. 24, foam insert 530 can be formed with recessed portions 532 that are configured to receive one or more modular support surface overlays 100 therein. Also, head rest 522 may be formed with a recessed portion 534 configured to receive different patient head support inserts 536 therein. Recessed portions 532 and 534 can act as nestable pockets that hold support surface overlays 100 and head supports 536 in place on the load-bearing device on which they are being used. Support surface overlays 100 can be used with different foam inserts 530 to conform to different load-bearing devices without the need to make countless different sizes and configurations of support surface overlays 100 for each different load-bearing device on which they will be used. Also, patient head supports 526 can be of different shapes and sizes to support heads of different sizes and shape and to provide different types of support.

8. Environmental Sensing

Figure 25E:
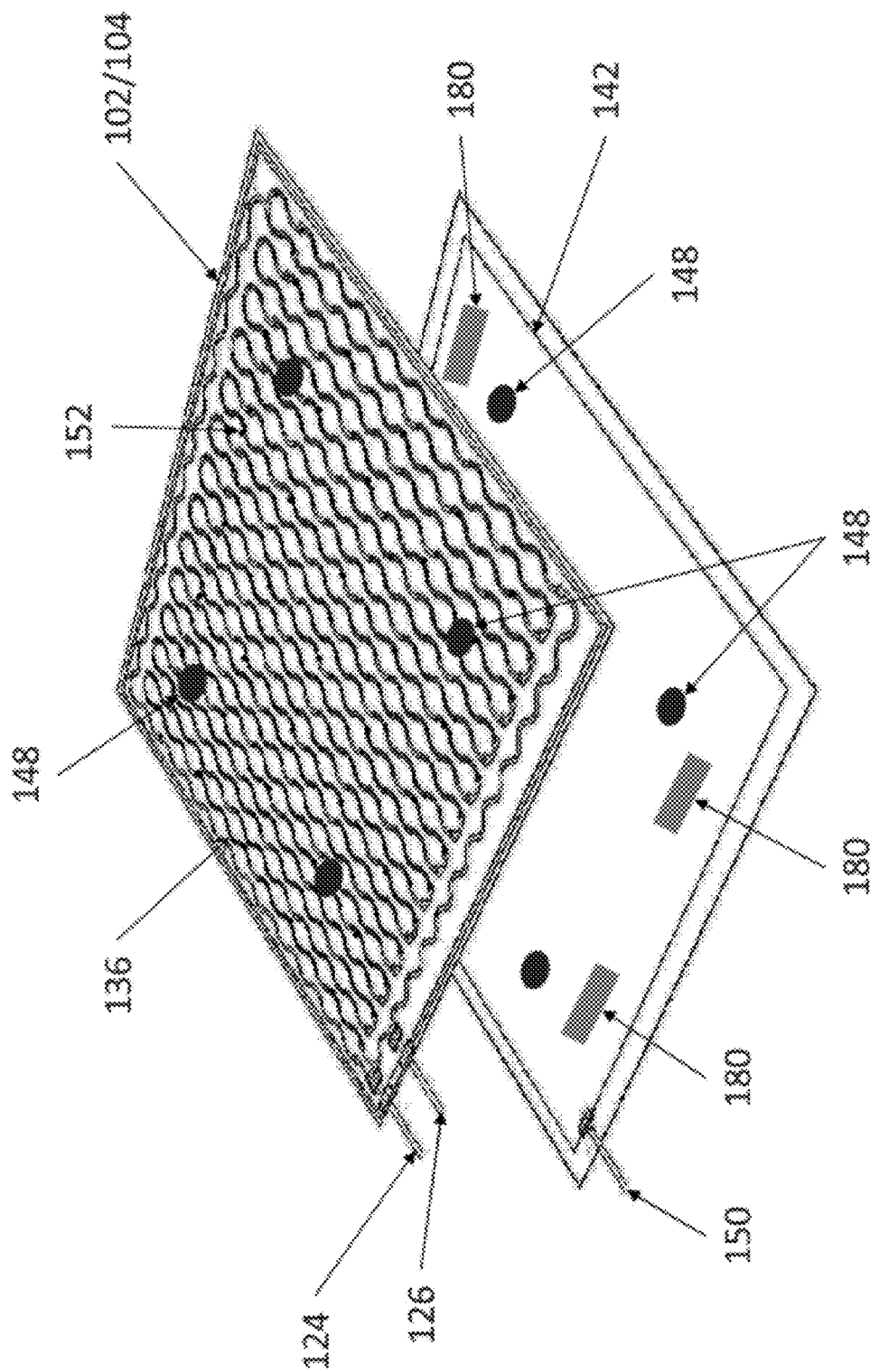
FIG. 25E is an exploded perspective view of the support surface overlay of FIG. 25A.

Capacitive, field effect, or other types of sensors could be incorporated into or attached to, for example, the upper and/or lower side of support surface overlay 100 to sense the presence of water, urine, feces, blood, or other contaminants that might be introduced to support surface overlay 100 during use. Alternatively, such sensors could be incorporated or attached to a layer attached to the underside of support surface overlay, for example, as described above in connection with the microclimate and/or anti-shear enhancements. Similar sensors could be incorporated into or attached to, for example, the upper and/or lower side of support surface overlay 100 to detect a bottom out condition wherein the load (for example, a user) disposed on support surface overlay 100 causes at least a portion of support surface overlay 100 to flatten out such that the load is supported directly by the underlying support surface instead of by contact nodes 122 of support surface overlay 100. FIG. 25E illustrates a sensor 180 incorporated into or disposed in third sheet 142 such that sensor 180 could be used to detect liquid or moisture intrusion into plenum 144 or a bottoming out condition. Also, thermocouples or other temperature sensing means could be provided to monitor the temperature about support surface overlay 100 and the region in which it interfaces with a user dispose thereon.

Such sensors could be electrically coupled to a monitoring system via electrical traces embedded within support surface overlay 100 or affixed to a surface thereof. Such a monitoring system could be incorporated into the ECU 404 of PCS 402 or otherwise into UIC 428 or it could be independent of same. Quick disconnect electrical connectors could be provided to facilitate electrical connections between support surface overlay 100 and the monitoring or control system.

9. Pressure Mapping

Support surface overlay 100 could be used in connection with pressure mapping technology in order to provide a user with information directed to the interface between support surface overlay 100 and a user lying thereon. For example, a pressure sensing mat (not shown) could be placed between support surface overlay 100 and an underlying bed, mat, mattress or other structure. The pressure sensing mat could provide output indicative of the interface pressure between support surface overlay 100 and a user at various points of contact by means of pressure transferred through support surface overlay 100 to the mat. Such a mapping system could be used to determine optimal inflation pressures for inflatable compartments 108, 110 and/or to detect a bottom out condition wherein a user disposed on support surface overlay 100 is overloading support surface overlay 100 such that the user is being supported by the underlayment under support surface overlay 100 instead of by contact nodes 122.

10. Use as Skin Pump

Support surface overlay 100 could be adapted for direct attachment by adhesive or other means to a user's body. Such direct attachment techniques could help maintain desired alignment and positioning support surface overlay 100 with respect to the user's body. To the extent not mitigated by the inclusion of relief cuts 136, operation of support surface overlay 100 when adhered directly to a user's body could have a pumping effect that might promote intersticial and other blood flow in the affected area of the user's body.

In other applications, support surface overlay 100 could be incorporated into a cast or support stocking to promote blood flow in the tissue of a wearer thereof.

11. Prosthetic Interface

Figure 28:
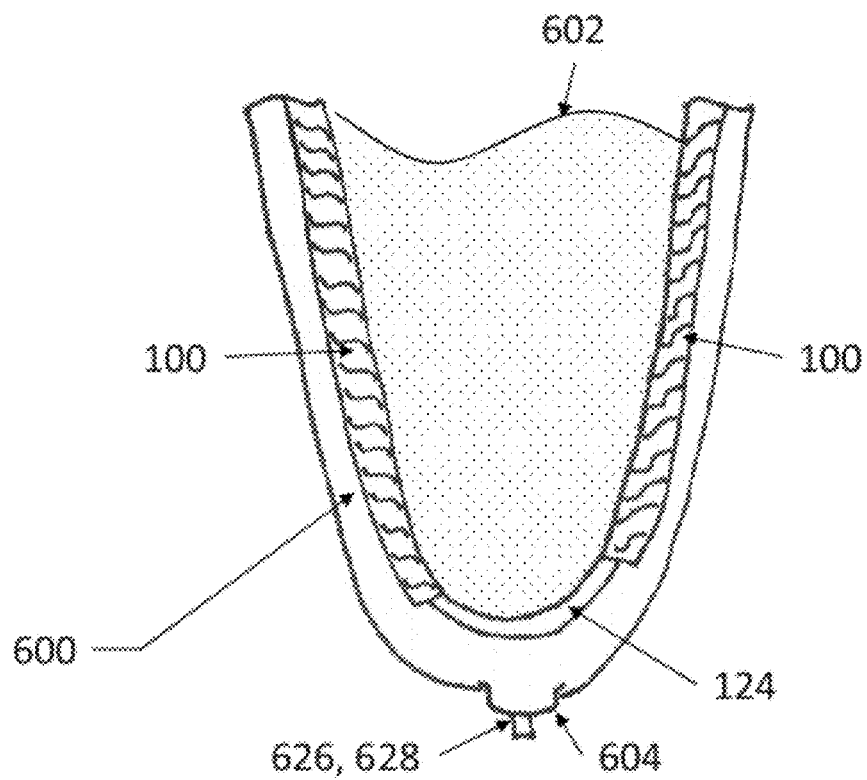
FIG. 28 is a cross-sectional side elevation view of a portion of a prosthetic device including a support surface overlay.

FIG. 28 illustrates a support surface overlay 100 disposed within the residual-limb receiving cup 600 of a prosthetic leg and adapted to receive residual limb 602. In this embodiment, support surface overlay 100 may include one or more inflatable compartments. Cup 600 may include a port 604 through which one or more fluid conduits 626, 628 corresponding to the one or more inflatable compartments may pass. Fluid conduits 626, 628 may be connected to a fluid pump or cylinder, for example, as discussed below.

Figure 29:
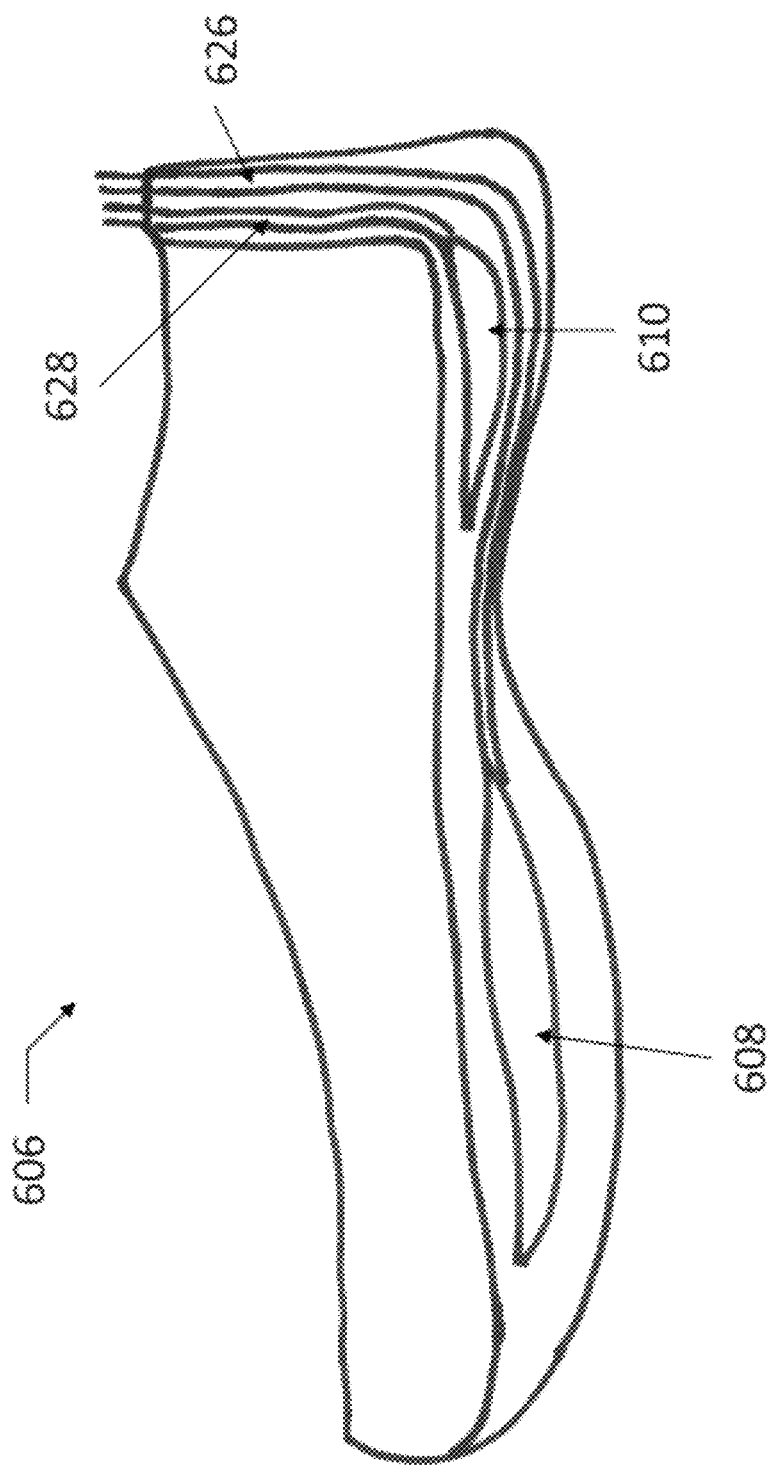
FIG. 29 is a cross-sectional side elevation view of a portion of a prosthetic device for use with support surface overlay of FIG. 28.

FIG. 29 shows a embodiment of a prosthetic foot 606 including a first bladder 608 located in the fore-region thereof and a second fluid-filled bladder 610 located in the heel region thereof. First and second bladders 608, 610 could be in fluid communication with corresponding inflatable compartments of one or more support surface overlays 100 disposed with limb-receiving cup 600. First bladder 608 tends to become compressed in response to a pressure applied to the fore-region of prosthetic foot 606 and de-compressed in response to removal of pressure thereto, as might occur during a normal walking activity. Similarly, second bladder 610 tends to become compressed in response to pressure applied to the heel region of prosthetic foot 606 and de-compressed in response to removal of pressure thereto.

First and second bladders 608, 610 could be in fluid communication with first and second inflatable compartments 108, 110, respectively, of support surface overlay 100 in cup 600 via fluid conduits 626, 628. The system defined thereby could be filled with a suitable fluid, for example, a silicone hydraulic fluid. As such, bladders 608, 610 could alternately pressurize and de-pressurize inflatable cells of inflatable compartments of support surface overlay(s) 100 in response to walking activity of a user wearing the apparatus.

Figure 30:
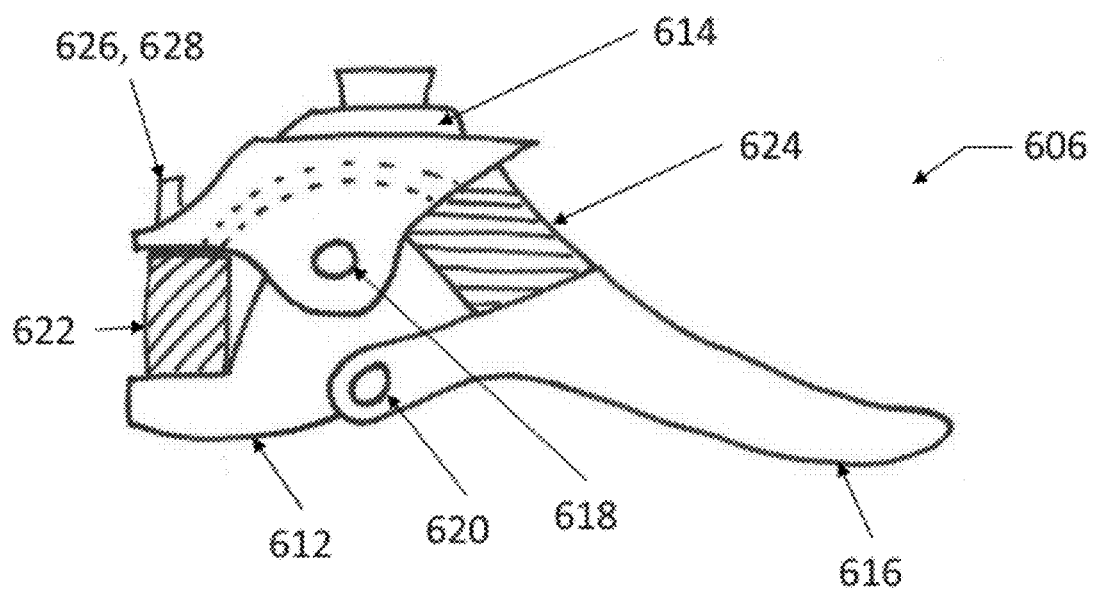
FIG. 30 is a cross-sectional side elevation view of a portion of another prosthetic device for use with support surface overlay of FIG. 28.

FIG. 30 shows another embodiment of a prosthetic foot 606 including first, second and third articulating elements 612, 614, 616 connected by pivot points 618, 620. A first fluid cylinder 622 is disposed between first and second articulating elements 612, 614 such that first fluid cylinder 622 and the fluid therein is alternately compressed and decompressed in response to articulation of first articulating element 612 with respect to second articulating element 614 as might occur during normal walking activity. Similarly, a second fluid cylinder 624 is disposed between second and third articulating elements 614, 616 such that second fluid cylinder 624 is alternately compressed and decompressed in response to articulation of second articulating element 614 with respect to third articulating element 616.

First and second fluid cylinders 622, 624 could be in fluid communication with first and second inflatable compartments 108, 110, respectively, of support surface overlay 100 in cup 600 via fluid conduits 626, 628. The system defined thereby could be filled with a suitable fluid, for example, a silicone hydraulic fluid. As such, fluid-filled bladders 608, 610 could alternately pressurize and de-pressurize inflatable cells of inflatable compartments of support surface overlay(s) 100 in response to walking activity of a user wearing the apparatus.

12. Operating Instructions

Support surface overlay 100 may be provided with operating instructions instructing a user to operate support surface overlay 100 in a manner that provides the Dabir effect. The instructions may be provided in a package including one or support surface overlays 100. Alternatively, such instructions may be provided separately in hard copy or, for example, electronically on a compact disc or through an Internet website.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A support surface overlay comprising:
a first flexible sheet;
a second flexible sheet joined to said first flexible sheet by at least one continuous, sinusoidally-shaped seam, said first flexible sheet, said second flexible sheet and said at least one seam defining a first selectively inflatable compartment comprising a plurality of inflatable cells arranged in a plurality of rows;
a first fluid conduit connecting an interior of said first selectively inflatable compartment with an exterior of said first selectively inflatable compartment in fluid communication; and
a first relief cut perforating said first flexible sheet and said second flexible sheet between a pair of said rows of inflatable cells, said first relief cut not perforating said at least a first selectively inflatable compartment, and said first relief cut extending continuously over at least about PI radians of said sinusoidally-shaped seam.

2. The support surface overlay of claim 1 further comprising a second relief cut between said first pair of said rows of inflatable cells, wherein an uncut portion separates said first relief cut from said second relief cut.

3. The support surface overlay of claim 2 wherein said second relief cut extends over at least about PI radians of said sinusoidally-shaped seam and said uncut portion extends over at least about PI radians of said sinusoidally-shaped seam.

4. The support surface overlay of claim 3 wherein said first relief cut extends over at least about five PI radians of said sinusoidally-shaped seam.

5. The support surface overlay of claim 1 further comprising a stress relief at an end of said first relief cut.

6. The support surface overlay of claim 1, wherein said second flexible sheet defines at least one aperture.

7. The support surface overlay of claim 6, said at least one aperture configured to allow controlled release therethrough of a medium from within said at least one selectively inflatable compartment and through an intersticial region defined by said inflatable cells.

8. The support surface overlay of claim 1, wherein said second flexible sheet comprises a permeable material configured to allow controlled release therethrough of a medium from within said at least one selectively inflatable compartment.

9. The support surface overlay of claim 8, said permeable material being sufficiently fluid-tight to allow for inflation of said inflatable compartments.

10. The support surface overlay of claim 1 further comprising a third flexible sheet joined to said first flexible sheet.

11. The support surface overlay of claim 10 further comprising a fourth flexible sheet joined to said second flexible sheet, said third and fourth flexible sheets defining a plenum.

12. The support surface overlay of claim 11 further comprising a fluid conduit in communication with an interior of said plenum and an exterior of said plenum.

13. The support surface overlay of claim 11, wherein said second flexible sheet comprises a permeable material configured to allow controlled release therethrough of a medium from within said at least one selectively inflatable compartment into said plenum or said second flexible sheet comprises at least one aperture configured to allow controlled release therethrough of a medium from within said at least one selectively inflatable compartment into said plenum.

14. The support surface overlay of claim 13 wherein said fourth flexible sheet comprises a permeable material configured to allow controlled release therethrough of a medium from within said plenum.

15. The support surface overlay of claim 1 further comprising an envelope about said first flexible sheet and said second flexible sheet.

16. The support surface overlay of claim 15 wherein said envelope is secured to at least one of said first flexible sheet and said second flexible sheet.

17. The support surface overlay of claim 15 wherein said envelope is secured to at least one of said first flexible sheet and said second flexible sheet at a perimeter region of said first flexible sheet and said second flexible sheet.

18. The support surface overlay of claim 15 wherein said envelope is secured to at least one of said first flexible sheet and said second flexible sheet distant from a perimeter region of said first flexible sheet and said second flexible sheet.

19. The support surface overlay of claim 15 wherein said envelope is substantially fluid tight.

20. The support surface overlay of claim 1, said first flexible sheet, said second flexible sheet, and said at least one seam further defining a second selectively inflatable compartment comprising a second plurality of inflatable cells, said first and second selectively inflatable compartments being selectively inflatable independent of one another.

21. The support surface overlay of claim 1, said plurality of inflatable cells being operable at inflation pressures of up to eight pounds per square inch.

22. The support surface overlay of claim 1, said plurality of inflatable cells being operable at inflation pressures of up to ten pounds per square inch.

23. The support surface overlay of claim 1, said plurality of inflatable cells defining corresponding contact nodes, said contact nodes having a nodal density of at least about two nodes per square decimeter.

24. The support surface overlay of claim 1, said relief cut being formed within the confines of said seam.

25. The support surface overlay of claim 1, said at least one seam being a welded seam comprising at least one weld line.

26. The support surface overlay of claim 1, said relief cut being configured to mitigate side-to-side contraction of said support surface overlay when said support surface overlay is inflated from a deflated condition to an inflated condition.

* * * * *